US007348009B1

(12) United States Patent
Bruck et al.

(10) Patent No.: US 7,348,009 B1
(45) Date of Patent: Mar. 25, 2008

(54) RECOMBINANT ALLERGEN WITH REDUCED ENZYMATIC ACTIVITY

(75) Inventors: Claudine Bruck, Rixensart (BE); Alex Bollen, Itterbeek (BE); Paul Jacobs, Lanquesaint (BE); Marc Georges Francis Massaer, Braine le Chateau (BE)

(73) Assignee: SmithKline Beecham Biologicals, s.a., Rixensart (BE)

( * ) Notice: Subject to any disclaimer, the term of this patent is extended or adjusted under 35 U.S.C. 154(b) by 0 days.

(21) Appl. No.: 09/554,860

(22) PCT Filed: Nov. 16, 1998

(86) PCT No.: PCT/EP98/07521

§ 371 (c)(1),
(2), (4) Date: May 19, 2000

(87) PCT Pub. No.: WO99/25823

PCT Pub. Date: May 27, 1999

(30) Foreign Application Priority Data

Nov. 19, 1997 (GB) ................................ 9724531.0

(51) Int. Cl.

| | |
|---|---|
| ***A61K 39/00*** | (2006.01) |
| ***A61K 38/28*** | (2006.01) |
| ***A01N 38/00*** | (2006.01) |
| ***C07K 1/00*** | (2006.01) |
| ***C07K 14/00*** | (2006.01) |
| ***C07K 17/00*** | (2006.01) |

(52) U.S. Cl. ........................ 424/185.1; 514/2; 530/350

(58) Field of Classification Search ................ 530/858, 530/868; 435/219; 424/185.1, 275.1
See application file for complete search history.

(56) References Cited

U.S. PATENT DOCUMENTS 5,762,943 A * 6/1998 Dolovich et al. ........ 424/275.1
6,287,559 B1 * 9/2001 King ....................... 424/94.62

FOREIGN PATENT DOCUMENTS

WO WO 94/05790 3/1994
WO 97/07218 2/1997

OTHER PUBLICATIONS

Topham et al. (Protein Engineering 1994; 7(7): 869-894.*
Smith et al. (Molecular Immunology 1996; 33(4/5): 399-405).*
Robinson et al., Clinical and Experimental Allergy, 1997, vol. 27, pp. 10-21.*
Forster et al., Journal of Allergy and Clinical Immunology, 1995, vol. 95, pp. 1229-1235.*
Creighton, T.E. 'Proteins Structures and Molecular Properties.' W.H. Freeman and Company: New York, 1993. pp. 79-81.*
Topham, et al., "Comparative Modelling of Major House Dust Mite Allergen *Der p* I: Structure Validation Using an Extended Environmental Amino Acid Propensity Table", *Protein Engineering*, 7(7): 869-894 (1994).
Hewitt, et al., "Heterogeneous Proteolytic Specificity and Activity of the House Dust Mite Proteinase Allergen *Der p* I", *Clinical and Experimental Allergy*, 27: 201-207 (1997).
Hewitt, et al., "A Major House Dust Mite Allergen Disrupts the Immunoglobulin E Network by Selectively Cleaving CD23: Innate Protection by Antiproteases", *J. Exp. Med.*, 182: 1537-1544 (1995).
Chua, et al., International Arch Allergy Immunol., vol. 101 pp. 364-368 (1993).
NCBI Accession No. P08176(DerP1) 9 pages.
Robinson, et al., *Clinical ad Experimental Allergy*, vol. 27 pp. 10-21 (1997).
Barrett, et al., *Handbook of Proteolytic Enzymes*, Ch. 186 pp. 546-555 Oct. 13, 1998.
Groves, et al., *Structure*, vol. 4 pp. 1193-1203 (1996).
Chua, et al., *J. Exp. Med.*, vol. 167 pp. 175-182 (1988).
Schultz, et al., *J. Exp. Med.*, vol. 187(2) pp. 271-275 (1998).
Carmona, et al., *Biochemistry*, vol. 35 pp. 8149-8157 (1996).
Jahn-Schmid, et al., *Immunotechnology*, vol. 2 pp. 103-113 (1996).

* cited by examiner

*Primary Examiner*—Maher M. Haddad
*Assistant Examiner*—Nora M. Rooney
(74) *Attorney, Agent, or Firm*—Jason C. Fedon; Edward R. Gimmi

(57) ABSTRACT

The present invention provides a novel treatment for allergy comprising a recombinant allergen with reduced enzymatic activity, thereby reducing the potential for an allergic response upon contact with a wild-type allergen.

4 Claims, 17 Drawing Sheets

FIGURE 1: Expression of a 43 kDa protein corresponding to mature Der p1 in fusion with the prepeptide MF-alpha of *Pichia pastoris* (construct pNIV4811) in yeast cells. The culture supernatants from various *Pichia pastoris* clones incubated in the absence or presence of methanol (methanol induction for 1 to 5 days indicated on the x axis) have been analyzed by SDS-PAGE and immunoblot analysis using an anti-Der p1 peptide (117-133) polyclonal antibody.

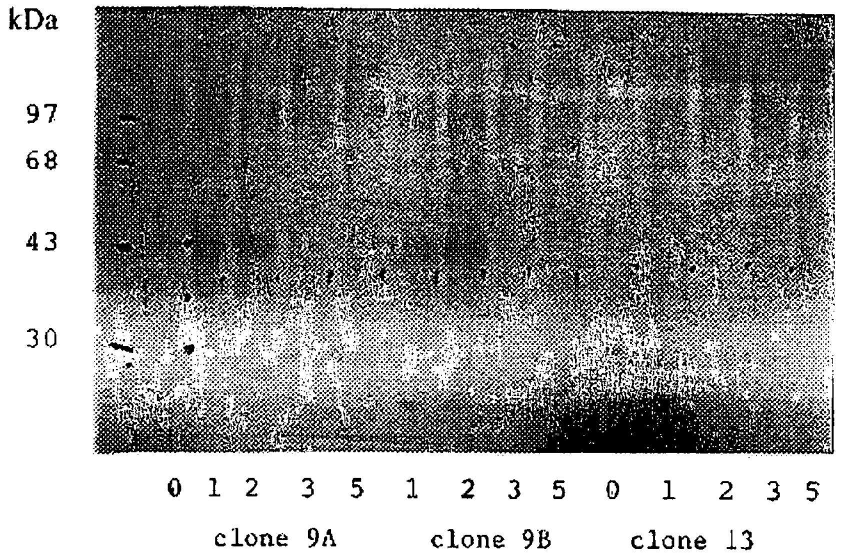

Figure 1

FIGURE 2: Expression of mature Der p1 (30 kDa) in fusion with the prepeptide of *Pichia pastoris* MF-alpha (construct pNIV4817) in yeast cells. The culture supernatants from *Pichia pastoris* cells incubated in the absence (J0) or presence of methanol for 1 day (J1) have been concentrated 50 times and, then, analyzed by SDS-PAGE and immunoblot analysis using an anti-Der p1 peptide (117-133) polyclonal antibody. Arrows indicate the mature Der p1 doublet at about 30 kDa

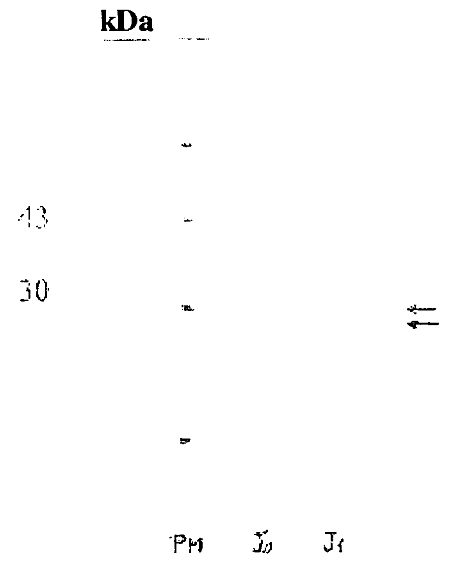

Figure 2

FIGURE 3: Expression of Der p1 in fusion with its propeptide (construct pNIV4812) in CHO-K1 cells. The cell extracts from different clones of CHO-K1 cells transfected with pNIV4812 (lanes 3-8) or transfected with the vector pEE14 alone as negative controls (lane 1 & 2) have been analyzed by SDS-PAGE and immunoblot analysis using an anti-Der p1 peptide (117-133) polyclonal antibody. The arrow indicates the mature Der p1 protein.

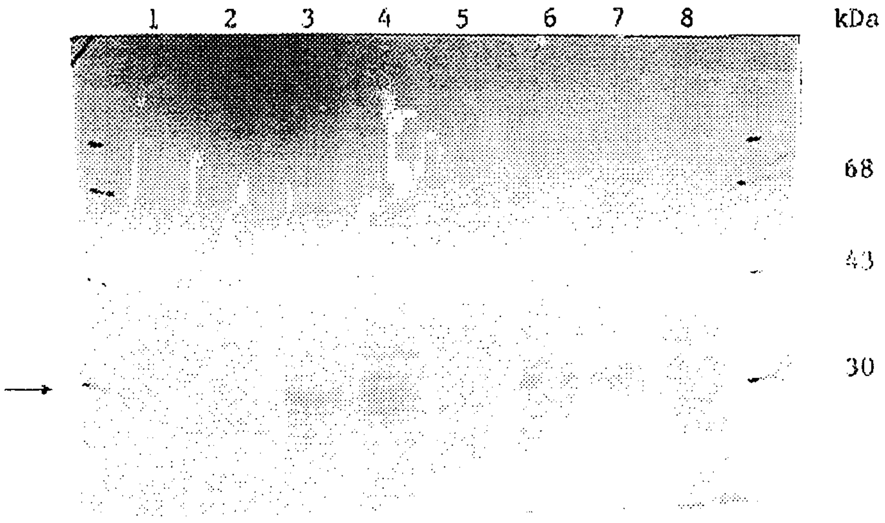

Figure 3

FIGURE 4: Expression of Der p1 in fusion with its propeptide (construct pNIV4840) in drosophila cells S2 (Invitrogen). The cell extracts of different clones of CHO-K1 cells transfected with pNIV4840 (lanes 1 & 4) or transfected with the inducible vector pMT/V5-His alone as negative controls (lanes 2,3,5, & 6) have been analyzed by SDS-PAGE and immunoblot analysis using an anti-Der p1 peptide (117-133) polyclonal antibody. The induction has been carried out for 22 hours (1-3) and 28 hours (4-6).

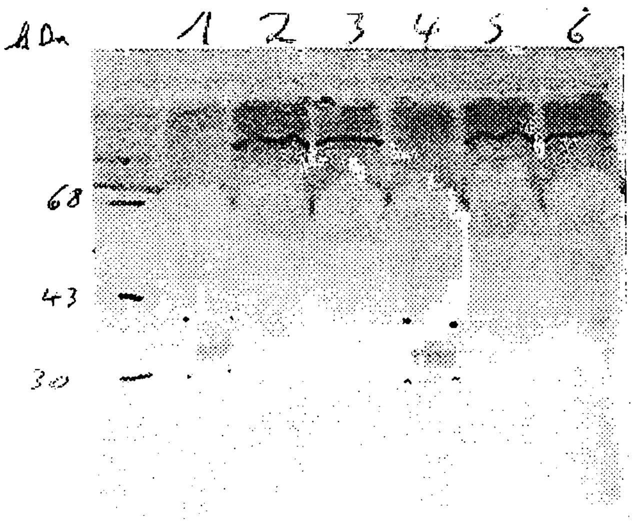

Figure 4

FIGURE 5: Expression of non-cleavable, non-activable Der p1 mutant in fusion with its pro-peptide (construct pNIV4842) in drosophila cells S2 (Invitrogen). The cell supernatants from transiently transfected S2 cells with pNIV4842 (lanes 1-4) or transfected with the inducible vector pMT/V5-His alone as negative control (lanes 5) have been analyzed by SDS-PAGE and immunoblot analysis using an anti-Der p1 peptide (117-133) polyclonal antibody. Lanes 1 to 4 correspond to 1, 4, 5, and 6 days of induction, respectively. Arrows indicate the pro Der p1 doublet at about 36 kDa.

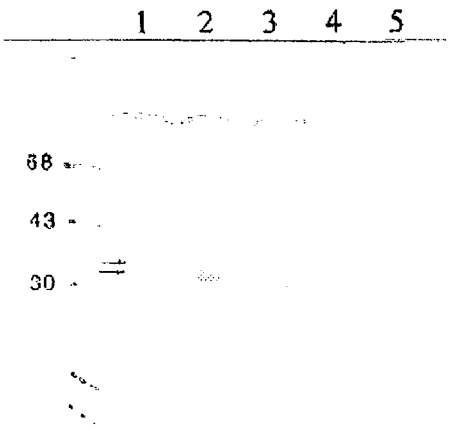

Figure 5

FIGURE 6: Expression of non-active Der p1 mutant in fusion with its propeptide (construct pNIV4843) in drosophila cells S2. The cell supernatants from transiently transfected S2 cells with pNIV4843 (lanes 6-9) or transfected with the inducible vector pMT/V5-His alone as negative control (lanes 5) have been analyzed by SDS-PAGE and immunoblot analysis using an anti-Der p1 peptide (117-133) polyclonal antibody. Lanes 6 to 9 correspond to 1, 4, 5, and 6 days of induction, respectively. Arrows indicate the mature Der p1 doublet at about 36 kDa

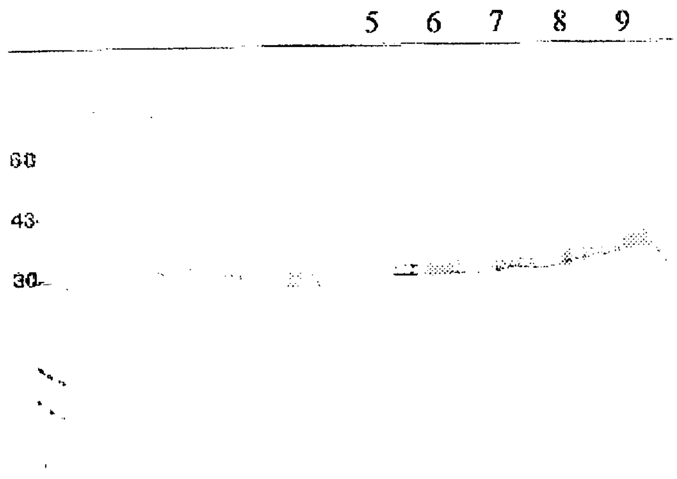

Figure 6

FIGURE 7: DerP1 restriction map of SEQ ID NO. 6.

```
(Linear) MAP of: Derp1.seq  check: 7532  from: 1  to: 963

ID   DP11695    standard; RNA; INV; 1099 BP.

                    BccI
                 CviJI |
                  HaeI |
                HaeIII |                      HaeII
                  MscI |                      HhaI|
    Tsp509I       EaeI ||             Eco47III|| CjePI
                         |      MnlI   MwoI  ||| MwoI|     BccI
     ATGAAAATTGTTTTGGCCATCGCCTCATTGTTGGCATTGAGCGCTGTTTATGCTCGTCCA
   1 ---------+---------+---------+---------+---------+---------+ 60
     TACTTTTAACAAAACCGGTAGCGGAGTAACAACCGTAACTCGCGACAAATACGAGCAGGT

a    M  K  I  V  L  A  I  A  S  L  L  A  L  S  A  V  Y  A  R  P  -

        DpnI
    Sau3AI |                                                 BbvI
     ClaI|                      CviJI                        NspV|
     TaqI|             CjePI  MboII                          TaqI|
     TCATCGATCAAAACTTTTGAAGAATACAAAAAAGCCTTCAACAAAAGTTATGCTACCTTC
  61 ---------+---------+---------+---------+---------+---------+ 120
     AGTAGCTAGTTTTGAAAACTTCTTATGTTTTTTCGGAAGTTGTTTTCAATACGATGGAAG

a    S  S  I  K  T  F  E  E  Y  K  K  A  F  N  K  S  Y  A  T  F  -

                   Sth132I
                MboII  |
               BscGI|  |
          Fnu4HI  ||   |
            AluI| ||   |
           CviJI| ||   |
           MboII| ||   |    HinfI
            TseI| ||   |     TfiI                    MnlI
     GAAGATGAAGAAGCTGCCCGTAAAAACTTTTTGGAATCAGTAAAATATGTTCAATCAAAT
 121 ---------+---------+---------+---------+---------+---------+ 180
     CTTCTACTTCTTCGACGGGCATTTTTGAAAAACCTTAGTCATTTTATACAAGTTAGTTTA

a    E  D  E  E  A  A  R  K  N  F  L  E  S  V  K  Y  V  Q  S  N  -

        BccI
     Hin4I |
     NgoGV |                             ApoI
     NlaIV |                            EcoRI
     BanI| |  MmeI Hpy188IX           Tsp509I     FokI
     GGAGGTGCCATCAACCATTTGTCCGATTTGTCGTTGGATGAATTCAAAAACCGATTTTTG
 181 ---------+---------+---------+---------+---------+---------+ 240
     CCTCCACGGTAGTTGGTAAACAGGCTAAACAGCAACCTACTTAAGTTTTTGGCTAAAAAC

a    G  G  A  I  N  H  L  S  D  L  S  L  D  E  F  K  N  R  F  L  -

          AluI              MnlI
         CviJI           Tsp509I
      HindIII |         BcgI  |
    CviRI   | |     BsgI |    |TaqI          BsmI
     ATGAGTGCAGAAGCTTTTGAACACCTCAAAACTCAATTCGATTTGAATGCTGAAACTAAC
 241 ---------+---------+---------+---------+---------+---------+ 300
     TACTCACGTCTTCGAAAACTTGTGGAGTTTTGAGTTAAGCTAAACTTACGACTTTGATTG
```

```
a      M  S  A  E  A  F  E  H  L  K  T  Q  F  D  L  N  A  E  T  N  -

BpmI, PstI, CviRI, Cac8I, SfcI, BcgI, CjePI, AluI, CviJI, MspA1I, PvuII, ClaI, TaqI,
CjePI, MwoI, BsaXI, AloI, PpiI, MaeIII, TaaI, Tsp45I

    GCCTGCAGTATCAATGGAAATGCTCCAGCTGAAATCGATTTGCGACAAATGCGAACTGTC
301 ---------+---------+---------+---------+---------+---------+ 360
    CGGACGTCATAGTTACCTTTACGAGGTCGACTTTAGCTAAACGCTGTTTACGCTTGACAG

a      A  C  S  I  N  G  N  A  P  A  E  I  D  L  R  Q  M  R  T  V  -

CviRI, MnlI, MslI, CviJI, DrdII, NlaIII, CviJI, AciI, Fnu4HI, TauI, BsbI

    ACTCCCATTCGTATGCAAGGAGGCTGTGGTTCATGTTGGGCTTTCTCTGGTGTTGCCGCA
361 ---------+---------+---------+---------+---------+---------+ 420
    TGAGGGTAAGCATACGTTCCTCCGACACCAAGTACAACCCGAAAGAGACCACAACGGCGT

a      T  P  I  R  M  Q  G  G  C  G  S  C  W  A  F  S  G  V  A  A  -

HinfI, TfiI, AluI, CviJI, CviJI, MwoI, TaaI, DpnI, BstYI, Sau3AI, AlwI, Tsp509I

    ACTGAATCAGCTTATTTGGCTTACCGTAATCAATCATTGGATCTTGCTGAACAAGAATTA
421 ---------+---------+---------+---------+---------+---------+ 480
    TGACTTAGTCGAATAAACCGAATGGCATTAGTTAGTAACCTAGAACGACTTGTTCTTAAT

a      T  E  S  A  Y  L  A  Y  R  N  Q  S  L  D  L  A  E  Q  E  L  -

TaqI, BsbI, TaaI, NlaIII, CjeI, BsaAI, FokI, PmlI, MaeII, HphI

    GTCGATTGTGCTTCCCAACACGGTTGTCATGGTGATACCATTCCACGTGGTATTGAATAC
481 ---------+---------+---------+---------+---------+---------+ 540
    CAGCTAACACGAAGGGTTGTGCCAACAGTACCACTATGGTAAGGTGCACCATAACTTATG

a      V  D  C  A  S  Q  H  G  C  H  G  D  T  I  P  R  G  I  E  Y  -

CjeI, MslI, BstXI, AluI, CviJI, MmeI, ClaI, TaqI, MaeII, BssSI, CviRI

    ATCCAACATAATGGTGTCGTCCAAGAAAGCTACTATCGATACGTTGCACGAGAACAATCA
541 ---------+---------+---------+---------+---------+---------+ 600
    TAGGTTGTATTACCACAGCAGGTTCTTTCGATGATAGCTATGCAACGTGCTCTTGTTAGT

a      I  Q  H  N  G  V  V  Q  E  S  Y  Y  R  Y  V  A  R  E  Q  S  -

NlaIII, CviRI, AclI, MaeII, ApoI, Tsp509I, CjeI

    TGCCGACGACCAAATGCACAACGTTTCGGTATCTCAAACTATTGCCAAATTTACCCACCA
601 ---------+---------+---------+---------+---------+---------+ 660
    ACGGCTGCTGGTTTACGTGTTGCAAAGCCATAGAGTTTGATAACGGTTTAAATGGGTGGT

a      C  R  R  P  N  A  Q  R  F  G  I  S  N  Y  C  Q  I  Y  P  P  -
```

```
AluI
CviJI
CjeI
HindIII
Hpy178III
ApoI
Tsp509I   CviJI   BcefI   HaeII HhaI Eco47III   RleAI

    AATGTAAACAAAATTCGTGAAGCTTTGGCTCAAACCCACAGCGCTATTGCCGTCATTATT
661 ---------+---------+---------+---------+---------+---------+ 720
    TTACATTTGTTTTAAGCACTTCGAAACCGAGTTTGGGTGTCGCGATAACGGCAGTAATAA

a   N  V  N  K  I  R  E  A  L  A  Q  T  H  S  A  I  A  V  I  I  -

CviJI
HaeIII
BccI
EaeI
GdiII
SfaNI   BsmI   HgaI   MslI   ThaI

    GGCATCAAAGATTTAGACGCATTCCGTCATTATGATGGCCGAACAATCATTCAACGCGAT
721 ---------+---------+---------+---------+---------+---------+ 780
    CCGTAGTTTCTAAATCTGCGTAAGGCAGTAATACTACCGGCTTGTTAGTAAGTTGCGCTA

a   G  I  K  D  L  D  A  F  R  H  Y  D  G  R  T  I  I  Q  R  D  -

BstEII                       MaeIII
MaeIII      HincII   MaeIII  TaaI   DraIII

    AATGGTTACCAACCAAACTATCACGCTGTCAACATTGTTGGTTACAGTAACGCACAAGGT
781 ---------+---------+---------+---------+---------+---------+ 840
    TTACCAATGGTTGGTTTGATAGTGCGACAGTTGTAACAACCAATGTCATTGCGTGTTCCA

a   N  G  Y  Q  P  N  Y  H  A  V  N  I  V  G  Y  S  N  A  Q  G  -

CjeI
TaaI
BciVI
CjePI
AlwI
RsaI
SunI
DpnI                  HgiEII                        CjeI
TaqI  Sau3AI          MunI                          TaaI
                      Tsp509I                       CjePI
                                                    HphI
                                                    BbvI
                                              MaeIII

    GTCGATTATTGGATCGTACGAAACAGTTGGGATACCAATTGGGGTGATAATGGTTACGGT
841 ---------+---------+---------+---------+---------+---------+ 900
    CAGCTAATAACCTAGCATGCTTTGTCAACCCTATGGTTAACCCCACTATTACCAATGCCA

a   V  D  Y  W  I  V  R  N  S  W  D  T  N  W  G  D  N  G  Y  G  -

                        Bsp24I
Fnu4HI    ClaI          CjePI     MboII
TseI      TaqI          CjeI      NdeI

    TATTTTGCTGCCAACATCGATTTGATGATGATTGAAGAATATCCATATGTTGTCATTCTC
901 ---------+---------+---------+---------+---------+---------+ 960
    ATAAAACGACGGTTGTAGCTAAACTACTACTAACTTCTTATAGGTATACAACAGTAAGAG

a   Y  F  A  A  N  I  D  L  M  M  I  E  E  Y  P  Y  V  V  I  L  -

    TAA
961 --- 963
    ATT
```

FIGURE 8: Sequence of full mutant DerP1 including pre-protein. Active site mutation Cys 132→Ala 132, corresponding to Cys34→Ala34 of the mature protein). Sequence includes coding (listed as SEQ ID NO. 6) and complementary DNA, and amino acid sequences (listed as SEQ ID NO. 1).

ATGAAAATTGTTTTGGCCATCGCCTCATTGTTGGCATTGAGCGCTGTTTATGCTCGTCCA 60
---------+---------+---------+---------+---------+---------+
TACTTTTAACAAAACCGGTAGCGGAGTAACAACCGTAACTCGCGACAAATACGAGCAGGT
M K I V L A I A S L L A L S A V Y A R P 20

TCATCGATCAAAACTTTTGAAGAATACAAAAAAGCCTTCAACAAAAGTTATGCTACCTTC 120
---------+---------+---------+---------+---------+---------+
AGTAGCTAGTTTTGAAAACTTCTTATGTTTTTTCGGAAGTTGTTTTCAATACGATGGAAG
S S I K T F E E Y K K A F N K S Y A T F 40

GAAGATGAAGAAGCTGCCCGTAAAAACTTTTTGGAATCAGTAAAATATGTTCAATCAAAT 180
---------+---------+---------+---------+---------+---------+
CTTCTACTTCTTCGACGGGCATTTTTGAAAAACCTTAGTCATTTTATACAAGTTAGTTTA
E D E E A A R K N F L E S V K Y V Q S N 60

GGAGGTGCCATCAACCATTTGTCCGATTTGTCGTTGGATGAATTCAAAAACCGATTTTTG 240
---------+---------+---------+---------+---------+---------+
CCTCCACGGTAGTTGGTAAACAGGCTAAACAGCAACCTACTTAAGTTTTTGGCTAAAAAC
G G A I N H L S D L S L D E F K N R F L 80

ATGAGTGCAGAAGCTTTTGAACACCTCAAAACTCAATTCGATTTGAATGCTGAAACTAAC 300
---------+---------+---------+---------+---------+---------+
TACTCACGTCTTCGAAAACTTGTGGAGTTTTGAGTTAAGCTAAACTTACGACTTTGATTG
M S A E A F E H L K T Q F D L N A E T N 100

GCCTGCAGTATCAATGGAAATGCTCCAGCTGAAATCGATTTGCGACAAATGCGAACTGTC 360
---------+---------+---------+---------+---------+---------+
CGGACGTCATAGTTACCTTTACGAGGTCGACTTTAGCTAAACGCTGTTTACGCTTGACAG
A C S I N G N A P A E I D L R Q M R T V 120

ACTCCCATTCGTATGCAAGGAGGCTGTGGTTCAGCTTGGGCTTTCTCTGGTGTTGCCGCA 420
---------+---------+---------+---------+---------+---------+
TGAGGGTAAGCATACGTTCCTCCGACACCAAGTCGAACCCGAAAGAGACCACAACGGCGT
T P I R M Q G G C G S A W A F S G V A A 140

ACTGAATCAGCTTATTTGGCTTACCGTAATCAATCATTGGATCTTGCTGAACAAGAATTA 480
---------+---------+---------+---------+---------+---------+
TGACTTAGTCGAATAAACCGAATGGCATTAGTTAGTAACCTAGAACGACTTGTTCTTAAT
T E S A Y L A Y R N Q S L D L A E Q E L 160

```
GTCGATTGTGCTTCCCAACACGGTTGTCATGGTGATACCATTCCACGTGGTATTGAATAC 540
---------+---------+---------+---------+---------+---------+
CAGCTAACACGAAGGGTTGTGCCAACAGTACCACTATGGTAAGGTGCACCATAACTTATG
V  D  C  A  S  Q  H  G  C  H  G  D  T  I  P  R  G  I  E  Y   180

ATCCAACATAATGGTGTCGTCCAAGAAAGCTACTATCGATACGTTGCACGAGAACAATCA 600
---------+---------+---------+---------+---------+---------+
TAGGTTGTATTACCACAGCAGGTTCTTTCGATGATAGCTATGCAACGTGCTCTTGTTAGT
I  Q  H  N  G  V  V  Q  E  S  Y  Y  R  Y  V  A  R  E  Q  S   200

TGCCGACGACCAAATGCACAACGTTTCGGTATCTCAAACTATTGCCAAATTTACCCACCA 660
---------+---------+---------+---------+---------+---------+
ACGGCTGCTGGTTTACGTGTTGCAAAGCCATAGAGTTTGATAACGGTTTAAATGGGTGGT
C  R  R  P  N  A  Q  R  F  G  I  S  N  Y  C  Q  I  Y  P  P   220

AATGTAAACAAAATTCGTGAAGCTTTGGCTCAAACCCACAGCGCTATTGCCGTCATTATT 720
---------+---------+---------+---------+---------+---------+
TTACATTTGTTTTAAGCACTTCGAAACCGAGTTTGGGTGTCGCGATAACGGCAGTAATAA
N  V  N  K  I  R  E  A  L  A  Q  T  H  S  A  I  A  V  I  I   240

GGCATCAAAGATTTAGACGCATTCCGTCATTATGATGGCCGAACAATCATTCAACGCGAT 780
---------+---------+---------+---------+---------+---------+
CCGTAGTTTCTAAATCTGCGTAAGGCAGTAATACTACCGGCTTGTTAGTAAGTTGCGCTA
G  I  K  D  L  D  A  F  R  H  Y  D  G  R  T  I  I  Q  R  D   260

AATGGTTACCAACCAAACTATCACGCTGTCAACATTGTTGGTTACAGTAACGCACAAGGT 840
---------+---------+---------+---------+---------+---------+
TTACCAATGGTTGGTTTGATAGTGCGACAGTTGTAACAACCAATGTCATTGCGTGTTCCA
N  G  Y  Q  P  N  Y  H  A  V  N  I  V  G  Y  S  N  A  Q  G   280

GTCGATTATTGGATCGTACGAAACAGTTGGGATACCAATTGGGGTGATAATGGTTACGGT 900
---------+---------+---------+---------+---------+---------+
CAGCTAATAACCTAGCATGCTTTGTCAACCCTATGGTTAACCCCACTATTACCAATGCCA
V  D  Y  W  I  V  R  N  S  W  D  T  N  W  G  D  N  G  Y  G   300

TATTTTGCTGCCAACATCGATTTGATGATGATTGAAGAATATCCATATGTTGTCATTCTC 960
---------+---------+---------+---------+---------+---------+
ATAAAACGACGGTTGTAGCTAAACTACTACTAACTTCTTATAGGTATACAACAGTAAGAG
Y  F  A  A  N  I  D  L  M  M  I  E  E  Y  P  Y  V  V  I  L   320

TAA
---
ATT
```

FIGURE 9: Sequence of full mutant DerP1 including pre-protein containing a deletion at the propeptide cleavage site (NAET). Sequence includes coding (listed as SEQ ID NO. 7) and complementary DNA, and amino acid sequences (listed as SEQ ID NO. 2).

```
ATGAAAATTGTTTTGGCCATCGCCTCATTGTTGGCATTGAGCGCTGTTTATGCTCGTCCA  60
---------+---------+---------+---------+---------+---------+
TACTTTTAACAAAACCGGTAGCGGAGTAACAACCGTAACTCGCGACAAATACGAGCAGGT
M  K  I  V  L  A  I  A  S  L  L  A  L  S  A  V  Y  A  R  P   20

TCATCGATCAAAACTTTTGAAGAATACAAAAAAGCCTTCAACAAAAGTTATGCTACCTTC  120
---------+---------+---------+---------+---------+---------+
AGTAGCTAGTTTTGAAAACTTCTTATGTTTTTTCGGAAGTTGTTTTCAATACGATGGAAG
S  S  I  K  T  F  E  E  Y  K  K  A  F  N  K  S  Y  A  T  F   40

GAAGATGAAGAAGCTGCCCGTAAAAACTTTTTGGAATCAGTAAAATATGTTCAATCAAAT  180
---------+---------+---------+---------+---------+---------+
CTTCTACTTCTTCGACGGGCATTTTTGAAAAACCTTAGTCATTTTATACAAGTTAGTTTA
E  D  E  E  A  A  R  K  N  F  L  E  S  V  K  Y  V  Q  S  N   60

GGAGGTGCCATCAACCATTTGTCCGATTTGTCGTTGGATGAATTCAAAAACCGATTTTTG  240
---------+---------+---------+---------+---------+---------+
CCTCCACGGTAGTTGGTAAACAGGCTAAACAGCAACCTACTTAAGTTTTTGGCTAAAAAC
G  G  A  I  N  H  L  S  D  L  S  L  D  E  F  K  N  R  F  L   80

ATGAGTGCAGAAGCTTTTGAACACCTCAAAACTCAATTCGATTTG           AAC  300
---------+---------+---------+---------+---------+---------+
TACTCACGTCTTCGAAAACTTGTGGAGTTTTGAGTTAAGCTAAAC           TTG
M  S  A  E  A  F  E  H  L  K  T  Q  F  D  L              N   100

GCCTGCAGTATCAATGGAAATGCTCCAGCTGAAATCGATTTGCGACAAATGCGAACTGTC  360
---------+---------+---------+---------+---------+---------+
CGGACGTCATAGTTACCTTTACGAGGTCGACTTTAGCTAAACGCTGTTTACGCTTGACAG
A  C  S  I  N  G  N  A  P  A  E  I  D  L  R  Q  M  R  T  V   120

ACTCCCATTCGTATGCAAGGAGGCTGTGGTTCATGTTGGGCTTTCTCTGGTGTTGCCGCA  420
---------+---------+---------+---------+---------+---------+
TGAGGGTAAGCATACGTTCCTCCGACACCAAGTACAACCCGAAAGAGACCACAACGGCGT
T  P  I  R  M  Q  G  G  C  G  S  C  W  A  F  S  G  V  A  A   140

ACTGAATCAGCTTATTTGGCTTACCGTAATCAATCATTGGATCTTGCTGAACAAGAATTA  480
---------+---------+---------+---------+---------+---------+
TGACTTAGTCGAATAAACCGAATGGCATTAGTTAGTAACCTAGAACGACTTGTTCTTAAT
T  E  S  A  Y  L  A  Y  R  N  Q  S  L  D  L  A  E  Q  E  L   160
```

```
GTCGATTGTGCTTCCCAACACGGTTGTCATGGTGATACCATTCCACGTGGTATTGAATAC 540
---------+---------+---------+---------+---------+---------+
CAGCTAACACGAAGGGTTGTGCCAACAGTACCACTATGGTAAGGTGCACCATAACTTATG
V  D  C  A  S  Q  H  G  C  H  G  D  T  I  P  R  G  I  E  Y   180

ATCCAACATAATGGTGTCGTCCAAGAAAGCTACTATCGATACGTTGCACGAGAACAATCA 600
---------+---------+---------+---------+---------+---------+
TAGGTTGTATTACCACAGCAGGTTCTTTCGATGATAGCTATGCAACGTGCTCTTGTTAGT
I  Q  H  N  G  V  V  Q  E  S  Y  Y  R  Y  V  A  R  E  Q  S   200

TGCCGACGACCAAATGCACAACGTTTCGGTATCTCAAACTATTGCCAAATTTACCCACCA 660
---------+---------+---------+---------+---------+---------+
ACGGCTGCTGGTTTACGTGTTGCAAAGCCATAGAGTTTGATAACGGTTTAAATGGGTGGT
C  R  R  P  N  A  Q  R  F  G  I  S  N  Y  C  Q  I  Y  P  P   220

AATGTAAACAAAATTCGTGAAGCTTTGGCTCAAACCCACAGCGCTATTGCCGTCATTATT 720
---------+---------+---------+---------+---------+---------+
TTACATTTGTTTTAAGCACTTCGAAACCGAGTTTGGGTGTCGCGATAACGGCAGTAATAA
N  V  N  K  I  R  E  A  L  A  Q  T  H  S  A  I  A  V  I  I   240

GGCATCAAAGATTTAGACGCATTCCGTCATTATGATGGCCGAACAATCATTCAACGCGAT 780
---------+---------+---------+---------+---------+---------+
CCGTAGTTTCTAAATCTGCGTAAGGCAGTAATACTACCGGCTTGTTAGTAAGTTGCGCTA
G  I  K  D  L  D  A  F  R  H  Y  D  G  R  T  I  I  Q  R  D   260

AATGGTTACCAACCAAACTATGCTGCTGTCAACATTGTTGGTTACAGTAACGCACAAGGT 840
---------+---------+---------+---------+---------+---------+
TTACCAATGGTTGGTTTGATAGTGCGACAGTTGTAACAACCAATGTCATTGCGTGTTCCA
N  G  Y  Q  P  N  Y  A  A  V  N  I  V  G  Y  S  N  A  Q  G   280

GTCGATTATTGGATCGTACGAAACAGTTGGGATACCAATTGGGGTGATAATGGTTACGGT 900
---------+---------+---------+---------+---------+---------+
CAGCTAATAACCTAGCATGCTTTGTCAACCCTATGGTTAACCCCACTATTACCAATGCCA
V  D  Y  W  I  V  R  N  S  W  D  T  N  W  G  D  N  G  Y  G   300

TATTTTGCTGCCAACATCGATTTGATGATGATTGAAGAATATCCATATGTTGTCATTCTC 960
---------+---------+---------+---------+---------+---------+
ATAAAACGACGGTTGTAGCTAAACTACTACTAACTTCTTATAGGTATACAACAGTAAGAG
Y  F  A  A  N  I  D  L  M  M  I  E  E  Y  P  Y  V  V  I  L   320

TAA
---
ATT
```

FIGURE 10: Sequence of full mutant DerP1 including pre-protein. Active site mutation His 268 → Ala 268, corresponding to His170→Ala170 of the mature protein). Sequence includes coding (listed as SEQ ID NO. 8) and complementary DNA, and amino acid sequences (listed as SEQ ID NO. 3).

```
ATGAAAATTGTTTTGGCCATCGCCTCATTGTTGGCATTGAGCGCTGTTTATGCTCGTCCA 60
---------+---------+---------+---------+---------+---------+
TACTTTTAACAAAACCGGTAGCGGAGTAACAACCGTAACTCGCGACAAATACGAGCAGGT
M  K  I  V  L  A  I  A  S  L  L  A  L  S  A  V  Y  A  R  P   20

TCATCGATCAAAACTTTTGAAGAATACAAAAAAGCCTTCAACAAAAGTTATGCTACCTTC 120
---------+---------+---------+---------+---------+---------+
AGTAGCTAGTTTTGAAAACTTCTTATGTTTTTTCGGAAGTTGTTTTCAATACGATGGAAG
S  S  I  K  T  F  E  E  Y  K  K  A  F  N  K  S  Y  A  T  F   40

GAAGATGAAGAAGCTGCCCGTAAAAACTTTTTGGAATCAGTAAAATATGTTCAATCAAAT 180
---------+---------+---------+---------+---------+---------+
CTTCTACTTCTTCGACGGGCATTTTTGAAAAACCTTAGTCATTTTATACAAGTTAGTTTA
E  D  E  E  A  A  R  K  N  F  L  E  S  V  K  Y  V  Q  S  N   60

GGAGGTGCCATCAACCATTTGTCCGATTTGTCGTTGGATGAATTCAAAAACCGATTTTTG 240
---------+---------+---------+---------+---------+---------+
CCTCCACGGTAGTTGGTAAACAGGCTAAACAGCAACCTACTTAAGTTTTTGGCTAAAAAC
G  G  A  I  N  H  L  S  D  L  S  L  D  E  F  K  N  R  F  L   80

ATGAGTGCAGAAGCTTTTGAACACCTCAAAACTCAATTCGATTTGAATGCTGAAACTAAC 300
---------+---------+---------+---------+---------+---------+
TACTCACGTCTTCGAAAACTTGTGGAGTTTTGAGTTAAGCTAAACTTACGACTTTGATTG
M  S  A  E  A  F  E  H  L  K  T  Q  F  D  L  N  A  E  T  N   100

GCCTGCAGTATCAATGGAAATGCTCCAGCTGAAATCGATTTGCGACAAATGCGAACTGTC 360
---------+---------+---------+---------+---------+---------+
CGGACGTCATAGTTACCTTTACGAGGTCGACTTTAGCTAAACGCTGTTTACGCTTGACAG
A  C  S  I  N  G  N  A  P  A  E  I  D  L  R  Q  M  R  T  V   120

ACTCCCATTCGTATGCAAGGAGGCTGTGGTTCATGTTGGGCTTTCTCTGGTGTTGCCGCA 420
---------+---------+---------+---------+---------+---------+
TGAGGGTAAGCATACGTTCCTCCGACACCAAGTACAACCCGAAAGAGACCACAACGGCGT
T  P  I  R  M  Q  G  G  C  G  S  C  W  A  F  S  G  V  A  A   140

ACTGAATCAGCTTATTTGGCTTACCGTAATCAATCATTGGATCTTGCTGAACAAGAATTA 480
---------+---------+---------+---------+---------+---------+
TGACTTAGTCGAATAAACCGAATGGCATTAGTTAGTAACCTAGAACGACTTGTTCTTAAT
T  E  S  A  Y  L  A  Y  R  N  Q  S  L  D  L  A  E  Q  E  L   160
```

GTCGATTGTGCTTCCCAACACGGTTGTCATGGTGATACCATTCCACGTGGTATTGAATAC 540
---------+---------+---------+---------+---------+---------+
CAGCTAACACGAAGGGTTGTGCCAACAGTACCACTATGGTAAGGTGCACCATAACTTATG
V D C A S Q H G C H G D T I P R G I E Y 180

ATCCAACATAATGGTGTCGTCCAAGAAAGCTACTATCGATACGTTGCACGAGAACAATCA 600
---------+---------+---------+---------+---------+---------+
TAGGTTGTATTACCACAGCAGGTTCTTTCGATGATAGCTATGCAACGTGCTCTTGTTAGT
I Q H N G V V Q E S Y Y R Y V A R E Q S 200

TGCCGACGACCAAATGCACAACGTTTCGGTATCTCAAACTATTGCCAAATTTACCCACCA 660
---------+---------+---------+---------+---------+---------+
ACGGCTGCTGGTTTACGTGTTGCAAAGCCATAGAGTTTGATAACGGTTTAAATGGGTGGT
C R R P N A Q R F G I S N Y C Q I Y P P 220

AATGTAAACAAAATTCGTGAAGCTTTGGCTCAAACCCACAGCGCTATTGCCGTCATTATT 720
---------+---------+---------+---------+---------+---------+
TTACATTTGTTTTAAGCACTTCGAAACCGAGTTTGGGTGTCGCGATAACGGCAGTAATAA
N V N K I R E A L A Q T H S A I A V I I 240

GGCATCAAAGATTTAGACGCATTCCGTCATTATGATGGCCGAACAATCATTCAACGCGAT 780
---------+---------+---------+---------+---------+---------+
CCGTAGTTTCTAAATCTGCGTAAGGCAGTAATACTACCGGCTTGTTAGTAAGTTGCGCTA
G I K D L D A F R H Y D G R T I I Q R D 260

AATGGTTACCAACCAAACTATGCTGCTGTCAACATTGTTGGTTACAGTAACGCACAAGGT 840
---------+---------+---------+---------+---------+---------+
TTACCAATGGTTGGTTTGATACGACGACAGTTGTAACAACCAATGTCATTGCGTGTTCCA
N G Y Q P N Y A A V N I V G Y S N A Q G 280

GTCGATTATTGGATCGTACGAAACAGTTGGGATACCAATTGGGGTGATAATGGTTACGGT 900
---------+---------+---------+---------+---------+---------+
CAGCTAATAACCTAGCATGCTTTGTCAACCCTATGGTTAACCCCACTATTACCAATGCCA
V D Y W I V R N S W D T N W G D N G Y G 300

TATTTTGCTGCCAACATCGATTTGATGATGATTGAAGAATATCCATATGTTGTCATTCTC 960
---------+---------+---------+---------+---------+---------+
ATAAAACGACGGTTGTAGCTAAACTACTACTAACTTCTTATAGGTATACAACAGTAAGAG
Y F A A N I D L M M I E E Y P Y V V I L 320

TAA
---
ATT

FIGURE 11: Amino acid sequence (SEQ ID NO: 4) for the mutant DerP1 as encoded by pNIV4842, and shown in figure 5.

1 MLLVNQSHQG FNKEHTSKMV SAIVLYVLLA AAAHSAFAAD PRPSSIKTFE

51 EYKKAFNKSY ATFEDEEAAR KNFLESVKYV QSNGGAINHL SDLSLDEFKN

101 RFLMSAEAFE HLKTQFDLNA CSINGNAPAE IDLRQMRTVT PIRMQGGCGS

151 CWAFSGVAAT ESAYLAYRNQ SLDLAEQELV DCASQHGCHG DTIPRGIEYI

201 QHNGVVQESY YRYVAREQSC RRPNAQRFGI SNYCQIYPPN ANKIREALAQ

251 THSAIAVIIG IKDLDAFRHY DGRTIIQRDN GYQPNYHAVN IVGYSNAQGV

301 DYWIVRNSWD TNWGDNGYGY FAANIDLMMI EEYPYVVIL*

FIGURE 12: Amino acid sequence (SEQ ID NO: 5) for the mutant DerP1 as encoded by pNIV4843, and shown in figure 6.

1 MLLVNQSHQG FNKEHTSKMV SAIVLYVLLA AAAHSAFAAD PRPSSIKTFE

51 EYKKAFNKSY ATFEDEEAAR KNFLESVKYV QSNGGAINHL SDLSLDEFKN

101 RFLMSAEAFE HLKTQFDLNA ETNACSINGN APAEIDLRQM RTVTPIRMQG

151 GCGSAWAFSG VAATESAYLA YRNQSLDLAE QELVDCASQH GCHGDTIPRG

201 IEYIQHNGVV QESYYRYVAR EQSCRRPNAQ RFGISNYCQI YPPNANKIRE

251 ALAQTHSAIA VIIGIKDLDA FRHYDGRTII QRDNGYQPNY HAVNIVGYSN

301 AQGVDYWIVR NSWDTNWGDN GYGYFAANID LMMIEEYPYV VIL*

RECOMBINANT ALLERGEN WITH REDUCED ENZYMATIC ACTIVITY

This application claims the benefit of §371 application of PCT/EP98/07521 filed 16 Nov. 1997.

The present invention relates to novel therapeutic formulations, said formulations being effective in the reduction of allergic responses to specific allergens. Further, this invention relates to novel polynucleotides, polypeptides encoded by them and to the use of such polynucleotides and polypeptides, and to their production. In particular, novel vaccines are provided comprising polypeptides and to their use in the treatment of humans suffering from allergies or prevention of individuals at risk from allergies, preferably said vaccines comprising a recombinant mutant *Dermatophagoides pteronyssinus* allergen Der P1.

Allergic responses in humans are common, and may be triggered by a variety of allergens. Allergic individuals are sensitised to allergens, and are characterised by the presence of high levels of allergen specific IgE in the serum, and possess allergen specific T-cell populations which produce Th2-type cytokines (IL-4, IL-5, and IL-13). Binding of IgE, in the presence of allergen, to Fc receptors present on the surface of mastocytes and basophils, leads to the rapid degranulation of the cells and the subsequent release of histamine, and other preformed and neoformed mediators of the inflammatory reaction. In addition to this, the stimulation of the T-cell recall response results in the production of IL-4 and IL-13, together cooperating to switch B-cell responses further towards allergen specific IgE production. For details of the generation of early and late phase allergic responses see Joost Van Neeven et al., 1996, Immunology Today, 17, 526. In non-allergic individuals, the immune response to the same antigens may additionally include Th1-type cytokines such as IFN-γ. These cytokines may prevent the onset of allergic responses by the inhibition of high levels of Th2-type immune responses, including high levels of allergen specific IgE. Importantly in this respect, is the fact that IgE synthesis may be controlled by an inhibitory feedback mechanism mediated by the binding of IgE/allergen complexes to the CD23 receptor on B-cells (Luo et al., J. Immunol., 1991, 146(7), 2122-9; Yu et al., 1994, Nature, 369(6483):753-6). In systems that lack cellular bound CD23, this inhibition of IgE synthesis does not occur. Current strategies in the treatment of such allergic responses include means to prevent the symptomatic effects of histamine release by anti-histamine treatments and/or local administration of anti-inflammatory corticosteroids. Other strategies which are under development include those which use the hosts immune system to prevent the degranulation of the mast cells, Stanworth et al., EP 0 477 231 B1. Other forms of immunotherapy have been described (Hoyne et al., J. Exp. Med., 1993, 178, 1783-1788; Holt et al., Lancet, 1994, 344, 456-458).

Some common allergens present in bee venom, house dust mite emanations and parasite proteins have been found to induce mast cell degranulation, and to stimulate interleukin-4 synthesis and secretion, even in the absence of allergen-specific IgE (Machado et al, 1996, Eur. J. Immunol. 26, 2972-2980). This non-immunological degranulation by proteolytic allergens, such as bee venom phospholipase A2 or proteases associated with house dust mite emanations is dependent on enzymatic activity.

The present invention provides recombinant mutant allergens having significantly reduced proteolytic activity relative to the wild-type proteolytically active allergen, as well as nucleic acids encoding the same, and their use as a prophylactic or immunotherapeutic agent against allergy. A preferred allergen is the house dust mite allergen Der p1.

The present invention relates to the provision of formulations for the treatment and prophylaxis of allergy, by providing means to down-regulate the production of IgE, as well as modifying the cell mediated response to the allergen, through a shift from a Th2 type to a Th1 type of response (as measured by the reduction of ratio of IL-4: IFN-γ producing DerP1 specific T-cells, or alternatively a reduction of the IL-5:IFN-γ ratio). This is achieved by the provision and use of recombinant mutant allergens with impaired enzymatic activity.

DerP1, a group 1 protease allergen of the house dust mite *Dermatophagoides pteronyssinus* (Topham et al., 1994, Protein Engineering, 7, 7, 869-894; Simpson et al., 1989, Protein Sequences and Data Analyses, 2, 17-21) is one such allergen. It is a 30 KDa protein and has been cloned and sequenced (Chua et al., 1988, J. Exp. Med., 167, 175-182). It is known to contain 222 amino acid residues in the mature protein. The sequence of DerP1 shares 31% homology to Papain, and importantly shares homology in the enzymatically active regions, most notably the Cys34-His170 ion pair (Topham et al., supra). DerP1 is produced in the mid-gut of the mite, where its role is probably related to the digestion of food. Up to 0.2 ng or proteolytically active DerP1 is incorporated into each fecal pellet, each around 10-40 μm in diameter and, therefore, easily inspired into the human respiratory tract. Overnight storage of purified DerP1 preparations at room temperature results in almost complete loss of enzymatic activity due to autoproteolytic degradation (Machado et al., 1996, Eur. J. Immunol. 26, 2972-2980).

DerP1 has been found to cleave the low affinity immunoglobulin IgE Fc receptor from the surface of human B lymphocytes (CD23, Hewitt et al., 1995, J. Exp. Med., 182, 1537-1544) and CD25 (Schultz et al., J. Exp. Med, 1998, 187(2):271-5) the alpha subunit of the human T cell interleukin-2 receptor. Cleavage of the receptor from the B cell surface was associated with a parallel increase in soluble CD23 in the culture supernatant. It has been suggested that the loss of cell surface CD23 from IgE-secreting B cells may promote and enhance IgE immune responses by ablating the important inhibitory feedback mechanism that normally limits IgE synthesis (Hewitt et al., 1995*, J. Exp. Med.,* 182, 1537-1544). Furthermore, since soluble CD23 has been shown to promote IgE production, fragments of CD23 released by DerP1 may directly enhance the synthesis of IgE. In addition to the effects of CD23 cleavage, the cleavage of CD25 from the surface of T-cells induces a decrease in proliferation and INF-gamma secretion, which, consequently, may bias the immune response toward a Th2 type response. Recent papers which relate to the DerP1 antigen are Machado et al. *Eur. J. Immunol.* (1996) 26: 2972-2980; Hewitt et al., *J. Exp. Med.* (1995) 182: 1537-1544; and Schulz et al. *Eur. J. Immunol.* (1995) 25: 3191-3194.

Other mutant allergens having reduced proteolytic activity which form part of the present invention may be based upon other group I cyteine proteases, such as Der f1 from *Dermatophagoides farinae* (80% homology to DerP1), as well as the groups III allergens (serine proteases) including DerpIII (Stewart et al., 1992, Immunology, 75, 29-35) and DerpIV (Yaseuda et al., 1993, Clin. Exp. Allergy, 23, 384-390); and the group IV allergens (amylases).

The allergens of the present invention are recombinantly produced. Der p1 proteolytic activity can be impaired by introducing mutations into the cDNA or genomic DNA, either at the enzymatically active site, or at the site of cleavage between the propeptide and the mature molecule.

Said mutant allergen having the following advantages over the wild-type allergen: 1) increases the Th1-type aspect of the immune responses in comparison to those stimulated by the wild type allergen, thereby leading to the suppression of allergic potential of the vaccinated host, and 2) having reduced allergenicity thus being more suitable for systemic administration of high doses of the immunogen, 3) will induce DerP1 specific IgG which compete with IgE for the binding of native DerP1.

The allergens of the present invention are also more stable than isolated or recombinant active DerP1, as measured by the lack of autoproteolytic degradation. Thus, the present invention also provides allergens which are stable compared to the wild-type form of the allergen, said allergens having significantly reduced proteolytic activity and being substantially full length proteins, optionally said allergens further comprising the pro-form of allergen.

One aspect of the present invention provides a nucleic acid encoding mutated Der p1 as set out above, and a further aspect of the invention provides mutated Der p1 per se. A yet further aspect of the present invention provides substantially stable recombinant DerP1. Said stable DerP1 being of substantially full length mature protein, or mature protein further comprising the pro-DerP1 section. The term "stable" in the context of the present invention is a product which does not undergo a substantial amount of decomposition by autoproteolysis when incubated overnight at room temperature in comparison to proteolytically active wild-type DerP1, as evidence by SDS PAGE analysis.

A still further aspect of the invention provides a process for the preparation of a mutated Der p1 protein, which process comprises expressing DNA encoding the said protein in a recombinant host cell and recovering the product.

A DNA molecule encoding a mutated Der p1 (or other mutated allergen) forms a further aspect of the invention and can be synthesized by standard DNA synthesis techniques, such as by enzymatic ligation as described by D. M. Roberts et al in Biochemistry 1985, 24, 5090-5098, by chemical synthesis, by in vitro enzymatic polymerization, or by a combination of these techniques.

Enzymatic polymerisation of DNA may be carried out in vitro using a DNA polymerase such as DNA polymerase I (Klenow fragment) in an appropriate buffer containing the nucleoside triphosphates dATP, dCTP, dGTP and dTTP as required at a temperature of 10°-37° C., generally in a volume of 50 ml or less. Enzymatic ligation of DNA fragments may be carried out using a DNA ligase such as T4 DNA ligase in an appropriate buffer, such as 0.05M Tris (pH 7.4), 0.01M $MgCl_2$, 0.01M dithiothreitol, 1 mM spermidine, 1 mM ATP and 0.1 mg/ml bovine serum albumin, at a temperature of 4° C. to ambient, generally in a volume of 50 ml or less. The chemical synthesis of the DNA polymer or fragments may be carried out by conventional phosphotriester, phosphite or phosphoramidite chemistry, using solid phase techniques such as those described in 'Chemical and Enzymatic Synthesis of Gene Fragments—A Laboratory Manual' (ed. H. G. Gassen and A. Lang), Verlag Chemie, Weinheim (1982), or in other scientific publications, for example M. J. Gait, H. W. D. Matthes, M. Singh, B. S. Sproat, and R. C. Titmas, Nucleic Acids Research, 1982, 10, 6243; B. S. Sproat and W. Bannwarth, Tetrahedron Letters, 1983, 24, 5771; M. D. Matteucci and M. H Caruthers, Tetrahedron Letters, 1980, 21, 719; M. D. Matteucci and M. H. Caruthers, Journal of the American Chemical Society, 1981, 103, 3185; S. P. Adams et al., Journal of the American Chemical Society, 1983, 105, 661; N. D. Sinha, J. Biernat, J. McMannus, and H. Koester, Nucleic Acids Research, 1984, 12, 4539; and H. W. D. Matthes et al., EMBO Journal, 1984, 3, 801.

Alternatively, the coding sequence can be derived from DerP1 mRNA, using known techniques (e.g. reverse transcription of mRNA to generate a complementary cDNA strand), and commercially available cDNA kits.

The invention is not limited to the specifically disclosed sequence, but includes any proteolytic allergen which has been mutated to remove some or all of its proteolytic activity, whilst retaining the ability to stimulate an immune response against the wild-type allergen. The proteolytic activity of the mutant allergens may be compared to the wild type by a CD23 cleavage assay according to Shultz et al., 1995, European Journal of Immunology, 25, 3191-3194), or enzymatic degradation of substrates described in Machado et al., 1996, Eur. J. Immunol., 26, 2972-2980. The immunogenicity of the mutant allergen may be compared to that of the wild-type allergen by various immunologicals assays. The cross-reactivity of the mutant and wild-type allergens may be assayed by in vitro T-cell assays after vaccination with either mutant or wild-type allergens. Briefly, splenic T-cells isolated from vaccinated animals may be restimulated in vitro with either mutant or wild-type allergen followed by measurement of cytokine production with commercially available ELISA assays, or proliferation of allergen specific T cells may be assayed over time by incorporation of tritiated thymidine. Also the immunogenicity may be determined by ELISA assay, the details of which may be easily determined by the man skilled in the art. Briefly, two types of ELISA assay are envisaged. First, to assess the recognition of the mutant DerP1 by sera of mice immunized with the wild type Der p1; and secondly by recognition of wild type DerP1 allergen by the sera of animals immunised with the mutant allergen. Briefly, each wells will be coated with 100 ng of purified wild type or mutated Der p1 overnight at 4° C. After incubating with a blocking solution (TBS-Tween 0.1% with 1% BSA) successive dilutions of sera will be incubated at 37° C. for 1 hour. The wells are washed 5 times, and total IgG revealed by incubating with an anti-IgG antibody conjugated with Alkaline phosphatase.

The reduction of enzymatically active allergen or DerP1 may be performed by introducing mutations into the native sequence before recombinantly producing the inactivated mutants. This may be achieved by: introducing substitutions, deletions, or additions into the active sites; by inserting, deleting, or substituting residues in regions of processing the inactive pro-enzyme into the active mature protein; or by altering the three dimensional structure of the protein such that enzymatic activity is lost, this may be achieved, amongst others, by expressing the protein in fragments, or by deleting cysteine residues involved in disulphide bridge formation, or by deleting or adding residues such that the tertiary structure of the protein is substantially altered. Alternatively, mutations may be generated with the effect of altering the interaction between the Cys and the His residues, at positions 34 and 170 of the mature protein respectively (corresponding to positions 132 and 268 of the pre-pro-protein respectively) in the resultant fully folded recombinant protein.

The invention is illustrated herein, but not limited to, three specific mutations which are are given as examples of proteolytically inactive DerP1. First, the enzymatic activity of DerP1 is abrogated by substituting a Cysteine residue in the active site for an alanine. This substitution occurs at Cys132→Ala132 of the pro-DerP1 protein sequence, and is set out in SEQ ID NO. 1. Second, the DerP1 allergen is recombinantly expressed and retained in its inactive proprotein form by deletion of four amino acid residues at the linker region between the pro- and mature proteins. This deletion removes amino acid residues NAET (SEQ ID NO. 31) from the site 96-99 inclusive, from the Pro-DerP1 protein sequence. This sequence is set out in SEQ ID NO. 2. Third, enzymatic activity of DerP1 is abrogated by substituting a Histidine residue in the active site for an alanine. This substitution occurs at His268→Ala268 of the pro-DerP1 protein sequence, and is set out in SEQ ID NO. 3.

The active sites of each wild-type enzymatic allergen may be determined from the literature, or by reference to homologues. For example, the active sites of DerP1, being a cysteine protease, may be putatively inferred by reference to other known cysteine proteases such as Papain. DerP1 shares essential structural and mechanistic features with other papain-like cysteine proteinases, including cathepsin B. The active site thiolate-imidazolium ion pair comprises the side chains of Cys34 and His 170 (Topham et al., 1994, Protein Engineering, 7, 7, 869-894).

Mutated versions of Der p 1 may be prepared by site-directed mutagenesis of the cDNA which codes for the Der p 1 protein by conventional methods such as those described by G. Winter et al in Nature 1982, 299, 756-758 or by Zoller and Smith 1982; Nucl. Acids Res., 10, 6487-6500, or deletion mutagenesis such as described by Chan and Smith in Nucl. Acids Res., 1984, 12, 2407-2419 or by G. Winter et al in Biochem. Soc. Trans., 1984, 12, 224-225.

The process of the invention may be performed by conventional recombinant techniques such as described in Maniatis et. al., Molecular Cloning—A Laboratory Manual; Cold Spring Harbor, 1982-1989.

In particular, the process may comprise the steps of:

1. Preparing a replicable or integrating expression vector capable, in a host cell, of expressing a DNA polymer comprising a nucleotide sequence that encodes the said mutant Der p1 protein;
2. Altering the enzymatic activity of the resultant protein by one of the following techniques: replacing the cysteine or histidine residues (or other residues interacting with other residues within the active site) from the active site with an alanine residue using site directed mutagenesis; replacement of a cDNA fragment by a pair of oligonucleotides whose sequence differ from the natural one; or alternatively, deleting four residues at the junction between the propeptide and the mature enzyme using site directed mutagenesis
3. Transforming a host cell with the said vector
4. Culturing the transformed host cell under conditions permitting expression of the DNA polymer to produce the protein; and
5. Recovering the protein.

The term 'transforming' is used herein to mean the introduction of foreign DNA into a host cell by transformation, transfection or infection with an appropriate plasmid or viral vector using e.g. conventional techniques as described in Genetic Engineering; Eds. S. M. Kingsman and A. J. Kingsman; Blackwell Scientific Publications; Oxford, England, 1988. The term 'transformed' or 'transformant' will hereafter apply to the resulting host cell containing and expressing the foreign gene of interest.

The expression vector is novel and also forms part of the invention.

The replicable expression vector may be prepared in accordance with the invention, by cleaving a vector compatible with the host cell to provide a linear DNA segment having an intact replicon, and combining said linear segment with one or more DNA molecules which, together with said linear segment encode the desired product, such as the DNA polymer encoding the Der p 1 protein under ligating conditions.

Thus, the DNA polymer may be preformed or formed during the construction of the vector, as desired.

The choice of vector will be determined in part by the host cell, which may be prokaryotic or eukaryotic. Suitable vectors include plasmids, bacteriophages, cosmids and recombinant viruses.

The preparation of the replicable expression vector may be carried out conventionally with appropriate enzymes for restriction, polymersation and ligation of the DNA, by procedures described in, for example, Maniatis et al cited above.

The recombinant host cell is prepared, in accordance with the invention, by transforming a host cell with a replicable expression vector of the invention under transforming conditions. Suitable transforming conditions are conventional and are described in, for example, Maniatis et al cited above, or "DNA Cloning" Vol. II, D. M. Glover ed., IRL Press Ltd, 1985.

The choice of transforming conditions is determined by the host cell. Thus, a bacterial host such as *E. coli* may be treated with a solution of $CaCl_2$ (Cohen et al, Proc. Nat. Acad. Sci., 1973, 69, 2110) or with a solution comprising a mixture of RbCl, $MnCl_2$, potassium acetate and glycerol, and then with 3-[N-morpholino]-propane-sulphonic acid, RbCl and glycerol. Mammalian cells in culture may be transformed by calcium co-precipitation of the vector DNA onto the cells, by lipofection, or by electroporation. The invention also extends to a host cell transformed with a replicable expression vector of the invention.

Culturing the transformed host cell under conditions permitting expression of the DNA polymer is carried out conventionally, as described in, for example, Maniatis et al and "DNA Cloning" cited above. Thus, preferably the cell is supplied with nutrient and cultured at a temperature below 45° C.

The product is recovered by conventional methods according to the host cell. Thus, where the host cell is bacterial, such as *E. coli* it may be lysed physically, chemically or enzymatically and the protein product isolated from the resulting lysate. Where the host cell is mammalian, the product may generally be isolated from the nutrient medium or from cell free extracts. Conventional protein isolation techniques include selective precipitation, absorption chromatography, and affinity chromatography including a monoclonal antibody affinity column.

Alternatively, the expression may be carried out either in insect cells using a suitable vector such as a baculovirus, in transformed *drosophila* cells, or mammalian CHO cells. The novel protein of the invention may also be expressed in yeast cells as described for the CS protein in EP-A-0 278 941.

The vaccine of the invention comprises an immunoprotective amount of the mutated version of the Der p1 (or other) allergenic protein. The term "immunoprotective" refers to the amount necessary to elicit an immune response against a subsequent challenge such that allergic disease is averted or mitigated. In the vaccine of the invention, an aqueous solution of the protein can be used directly. Alternatively, the protein, with or without prior lyophilization, can be mixed, adsorbed, or covalently linked with any of the various known adjuvants. Preferably, the adjuvant may be a preferential inducer of Th1-type immune responses.

An immune response is generated to an antigen through the interaction of the antigen with the cells of the immune system. The resultant immune response may be broadly distinguished into two extreme categories, being a humoral or cell mediated immune responses (traditionally characterised by antibody and cellular effector mechanisms of protection respectively). These categories of response have been termed Th1-type responses (cell-mediated response), and Th2-type immune responses (humoral response). In mice Th1-type responses are characterised by the generation of antibodies of the IgG2a subtype, whilst in the human these correspond to IgG1 type antibodies. Th2-type immune responses are characterised by the generation of a broad range of immunoglobulin isotypes including in mice IgE, IgG1, IgA, and IgM.

It can be considered that the driving force behind the development of these two types of immune responses are cytokines, a number of identified protein messengers which serve to help the cells of the immune system and steer the eventual immune response to either a Th1 or Th2 response. Thus Th1-type cytokines induce a cell mediated immune response to the given antigen, whilst Th2-type cytokines induce a humoral immune response to the antigen.

It is important to remember that the distinction of Th1 and Th2-type immune responses is not absolute. In reality an individual will support an immune response which is describe as being predominantly Th1 or predominantly Th2. However, it is often convenient to consider the families of cytokines in terms of that described in murine CD4 T cell clones by Mosmann and Coffman (Mosmann, T. R. and Coffman, R. L. (1989) *TH1 and TH2 cells: different patterns of lymphokine secretion lead to different functional properties. Annual Review of Immunology,* 7, p 145-173). Traditionally, Th1-type responses are associated with cell mediated effector mechanisms such as cytotoxic lymphocytes (CTL) and can be characterised by the production of the INF-γ and IL-2 cytokines by T-lymphocytes. Other cytokines often directly associated with the induction of Th1-type immune responses are not produced by T-cells, such as IL-12. In contrast, Th2-type responses are associated, with humoral mechanisms and the secretion of IL-4, IL-s, IL-6, IL-10 and tumour necrosis factor-β (TNF-β).

It is known that certain vaccine adjuvants are particularly suited to the stimulation of either Th1 or Th2-type cytokine responses. This weighting of cytokine production translates into the generation of either a predominantly Th1-type ot Th2-type immune responses. Traditionally the best indicators of the Th1:Th2 balance of the immune response after a vaccination or infection includes direct measurement of the production of Th1 or Th2 cytokines by T lymphocytes in vitro after restimulation with antigen, and measurement of the IgG1:IgG2a ratio of antigen specific antibody responses.

Thus, a Th1-type adjuvant is one which stimulates isolated T-cell populations to produce high levels of Th1-type cytokines when re-stimulated with antigen in vitro, and induces antigen specific immunoglobulin responses associated with Th1-type mechanisms (IgG2a in mice, IgG1 in the human).

Adjuvants include, but are not limited to, aluminium hydroxide, muramyl dipeptide and saponins such as Quil A, 3D-MPL (3-O-deacylated monophosphoryl lipid A), or TDM. As a further exemplary alternative, the protein can be encapsulated within microparticles such as liposomes. Particularly preferred adjuvants which preferentially stimulate Th1-type immune responses are combinations of 3D-MPL and QS21 (EP 0 671 948 B1), oil in water emulsions comprising 3D-MPL and QS21 (WO 95/17210), 3D-MPL formulated with other carriers (EP 0 689 454 B1), or QS21 formulated in cholesterol containing liposomes (WO 96/33739), or immunostimulatory oligonucleotides (WO 96/02555). In yet another exemplary alternative, the protein can be conjugated to a carrier protein which is capable of providing T-cell help to the generation of the anti-allergen immune response, such as tetanus toxoid. Use of Quil A is disclosed by Dalsgaard et al., *Acta Vet Scand,* 18:349 (1977).

BRIEF DESCRIPTION OF THE FIGURES

FIG. 1 illustrates the expression of a 43 kDa protein corresponding to mature Der p1 in fusion with the prepeptide MF-alpha of *Pichia pastoris* (construct pNIV4811) in yeast cells. The culture supernatants from various *Pichia pastoris* clones incubated in the absence or presence of methanol (methanol induction for 1 to 5 days indicated on the x axis) have been analyzed by SDS-PAGE and immunoblot analysis using an anti-Der p1 peptide (117-133) polyclonal antibody.

FIG. 2 illustrates expression of mature Der p1 (30 kDa) in fusion with the prepeptide of *Pichia pastoris* MF-alpha (construct pNIV4817) in yeast cells. The culture supernatants from *Pichia pastoris* cells incubated in the absence (J0) or presence of methanol for 1 day (J1) have been concentrated 50 times and, then, analyzed by SDS-PAGE and immunoblot analysis using an anti-Der p1 peptide (117-133) polyclonal antibody. Arrows indicate the mature Der p1 doublet at about 30 kDa.

FIG. 3 illustrates expression of Der p1 in fusion with its propeptide (construct pNIV4812) in CHO-K1 cells. The cell extracts from different clones of CHO-K1 cells transfected with pNIV4812 (lanes 3-8) or transfected with the vector pEE14 alone as negative controls (lane 1 & 2) have been analyzed by SDS-PAGE and immunoblot analysis using an anti-Der p1 peptide (117-133) polyclonal antibody. The arrow indicates the mature Der p1 protein.

FIG. 4 illustrates expression of Der p1 in fusion with its propeptide (construct pNIV4840) in *drosophila* cells S2 (Invitrogen). The cell extracts of different clones of CHO-K1 cells transfected with pNIV4840 (lanes 1 & 4) or transfected with the inducible vector pMT/V5-His alone as negative controls (lanes 2, 3, 5, & 6) have been analyzed by SDS-PAGE and immunoblot analysis using an anti-Der p1 peptide (117-133) polyclonal antibody. The induction has been carried out for 22 hours (1-3) and 28 hours (4-6).

FIG. 5 illustrates expression of non-cleavable, non-activable Der p1 mutant in fusion with its pro-peptide (construct pNIV4842) in *drosophila* cells S2 (Invitrogen). The cell supernatants from transiently transfected S2 cells with pNIV4842 (lanes 1-4) or transfected with the inducible vector pMT/V5-His alone as negative control (lanes 5) have been analyzed by SDS-PAGE and immunoblot analysis using an anti-Der p1 peptide (117-133) polyclonal antibody. Lanes 1 to 4 correspond to 1, 4, 5, and 6 days of induction, respectively. Arrows indicate the pro Der p1 doublet at about 36 kDa.

FIG. 6 illustrates expression of non-active Der p1 mutant in fusion with its propeptide (construct pNIV4843) in *drosophila* cells S2. The cell supernatants from transiently transfected S2 cells with pNIV4843 (lanes 6-9) or transfected with the inducible vector pMT/V5-His alone as negative control (lanes 5) have been analyzed by SDS-PAGE and immunoblot analysis using an anti-Der p1 peptide (117-133) polyclonal antibody. Lanes 6 to 9 correspond to 1, 4, 5, and 6 days of induction, respectively. Arrows indicate the mature Der p1 doublet at about 36 kDa.

FIG. 7 illustrates DerP1 restriction map of SEQ ID NO. 6.

FIG. 8 illustrates sequence of full mutant DerP1 including pre-protein. Active site mutation Cys 132→Ala 132, corresponding to Cys34→eAla34 of the mature protein).

Sequence includes coding (listed as SEQ ID NO. 6) and complementary DNA, and amino acid sequences (listed as SEQ ID NO. 1).

FIG. 9 illustrates sequence of full mutant DerP1 including pre-protein containing a deletion at the propeptide cleavage site (NAET). Sequence includes coding (listed as SEQ ID NO. 7) and complementary DNA, and amino acid sequences (listed as SEQ ID NO. 2).

FIG. 10 illustrates sequence of full mutant DerP1 including pre-protein. Active site mutation His 268→Ala 268, corresponding to His170→Ala170 of the mature protein). Sequence includes coding (listed as SEQ ID NO. 8) and complementary DNA, and amino acid sequences (listed as SEQ ID NO. 3).

FIG. 11 illustrates amino acid sequence (SEQ ID NO: 4) for the mutant DerP1 as encoded by pNIV4842, and shown in FIG. 5.

FIG. 12 illustrates amino acid sequence (SEQ ID NO: 5) for the mutant DerP1 as encoded by pNIV4843, and shown in FIG. 6.

Vaccine preparation is generally described in *New Trends and Developments in Vaccines*, Voller et al. (eds.), University Park Press, Baltimore, Md., 1978. Encapsulation within liposomes is described by Fullerton, U.S. Pat. No. 4,235,877. Conjugation of proteins to macromolecules is disclosed, for example, by Likhite, U.S. Pat. No. 4,372,945 and Armor et al., U.S. Pat. No. 4,474,757.

The amount of the protein of the present invention present in each vaccine dose is selected as an amount which induces an immunoprotective response without significant, adverse side effects in typical vaccines. Such amount will vary depending upon which specific immunogen is employed and whether or not the vaccine is adjuvanted. Generally, it is expected that each dose will comprise 1-1000 μg of protein, preferably 1-200 μg. An optimal amount for a particular vaccine can be ascertained by standard studies involving observation of antibody titres and other responses in subjects. Following an initial vaccination, subjects will preferably receive a boost in about 4 weeks, followed by repeated boosts every six months for as long as a risk of allergic responses exists.

The vaccines of the present invention may be administered to adults or infants, however, it is preferable to vaccinate individuals soon after birth before the establishment of substantial Th2-type memory responses.

A further aspect of the invention provides a method of preventing or mitigating an allergic disease in man, which method comprises administering to a subject in need thereof an immunogenically effective amount of a mutated allergen of the invention, or of a vaccine in accordance with the invention.

The examples which follow are illustrative but not limiting of the invention. Restriction enzymes and other reagents were used substantially in accordance with the vendors' instructions.

EXAMPLE 1

Expression in *Pichia pastoris*

Construction of pNIV4811 pNIV4811 is designed to promote the expression of mature Der p1 in fusion with the prepropeptide of *Pichia pastoris* MFα. Plasmid ATCC87307 contains the sequence for mature DerP1. The full Derpl restriction map is given in FIG. 7.

Ligate with T4 DNA Ligase:
SphI-XhoI from pPIC9k (INVITROGEN V175-20)
XhoI-PstI oligonucleotides whose sequences follow (no 97038 and no 97039)
PstI-XbaI from pNIV4810 (plasmid ATCC87307)
AvrII-SphI from pPIC9k
Sequences of the Oligonucleotides:
no. 97038 (SEQ ID NO. 9)
5'TCGAGAAAAGAGAGGCTGAAGCTAC-TAACGCCTGCA3'
no. 97039 (SEQ ID NO. 10)
5'GGCGTTAGTAGCTTCAGCCTCTCTTTTC3'

Results

*Pichia Pastoris* transfected with pNIV4811 leads to the expression of a protein of 43 kD, comprising uncleaved proMFα-mature Der p1 fusion protein, has been detected in several clones (FIG. 1).

Construction of pNIV4817 pNIV4817 is derived from pNIV4811. It is designed to promote the expression of the mature Der p1 in fusion with the prepeptide of *Pichia pastoris* MFα.

Ligate: BstEII-BamHI from pNIV4811
BamHI-PstI oligonucleotides no. 97262 and no. 97263 whose sequence follows
PstI-BstEII from pNIV4811

Sequences of the Oligonucleotides
no. 97262 (SEQ ID NO. 11)
5'GATCCAAACGATGAGATTTCCT-TCAATTTTTACTGCAGTTTTATTCGC AGC ATCCTC-CGCATTAGCTGCTCCAACTAACGCCTGCA3'
no. 97263 (SEQ ID NO. 12)
5'GGCGTTAGTTGGAGCAGCTAATGCGGAG-GATGCTGCGAATAAAACTGC AGTAAAAATTGAAG-GAAATCTCATCGTTTG3'

Results

Several clones expressed the mature form of Der p1 protein with an apparent molecular weight of 30 kDa, which was secreted into the supernatant (FIG. 2).

Construction of pNIV4815

Starting from pNIV4811, the following construction is designed to delete four residues [N-A-E-T (T is the first residue of the mature protein)] at the junction between the propeptide and the mature enzyme.

Ligate: BinI-BamHI fragment from pPIC9k (the vector used for expression in *P. pastoris*)
BamHI-EaeI fragment from pNIV4811
EaeI-EcoRI fragment generated by RT-PCR with primers No 97142 and 97143. Residues: $A_6$ to $E_{74}$.
EcoRI-PstI oligonucleotides whose sequence follows (No 97140 and 97141). Residues: F75 to C102 except N96AET99
PstI—XbaI fragment from pNIV4810.

```
Sequence of the oligonucleotides
allowing the NAET deletion:

No 97140 (SEQ ID NO. 13)                          75 bases
5' AATTCAAAAACCGATTTTTGATGAGTG-
CAGAAGCTTTTGAACACCTAAA
ACTCAATTCGATTTGAACGCCTGCA 3'

No 97141 (SEQ ID NO. 14)                          67 bases
5' GGCGTTCAAATCGAATTGAGTTTTGAG-
GTGTTCAAAAGCTTCTGCATCA
TCAAAAATCGGTTTTTG 3'
```

-continued

RT-PCR Primers

No 97142 (SEQ ID NO. 15) 25 bases
5' CATGAAAATTGTTTTGGCCATCGCC 3'
EaeI

No 97143 (SEQ ID NO. 16) 24 bases
5' CGGTTTTTGAATTCATCCAACGAC 3'
EcoRI

Construction of pNIV4819

Starting from pNIV4817, an expression plasmid designed to produce the mature form of Der p1 in *Pichia pastoris*, the following construction is made to replace the cysteine residue from the active by an alanine residue (corresponding to the Cys 34 mutation in the mature protein).

Ligate: Bpu11021-AseI fragment from pNIV4817

AseI-TfiI synthetic fragment resulting from hybridization of oligonucleotides no. 97121 and no. 97122 whose sequence follows: corresponding to residues $I_{104}$ to $E_{142}$ of the proDerP1 ($I_{6-}$ of mature DerP1 protein)

TfiI-BstEII fragment from pNIV4810 (ATCC 87307)

BstEII-Bpu 11021 fragment from pNIV4817

Sequences of the oligonucleotides no 97121 (SEQ ID NO. 17) Ala 113 bases
5' TAATGGAAATGCTCCAGCTGAAATC-GATTTGCGACAAATGCCACTCCCA
TTCGTATGCAAGGAGGCTGTGGTTCAGCTTGGTGTTGCCGCAACTG 3' no 97122 (SEQ ID NO. 18) 114 bases
5' ATTCAGTTGCGGCAACACCAGAGAAAGCCCAAAGCTGAACCACAGCCT
CCTTGCATACGAATGGGAGTGACAGTTCGCATTTGTCGCAAATCGATTTC
AGCTGGAGCATTTCCAT 3'

Construction of pNIV4815

Starting from pNIV4811, the following construction is made to delete four residues [N-A-E-T (T is the first residue of the mature protein)] at the junction between the propeptide and the mature enzyme.

Ligate: BlnI-BamHI fragment from pPIC9k (the vector used for expression in PPIChia pastoris)

BamHI—EaeI fragment from pIV4811

EaeI—EcoRI fragment generated by RT-PCR with primers

No. 97142 and 97143. Residues: $A_6$ to $E_{74}$.

EcoRI—PstI oligonucleotides whose sequence follows (No. 97140 and 97141). Residues: F75 to C102 except N96AET99

PstI—XbaI fragment from pNIV4810.

Sequence of the oligonucleotides: allowing the NAET deletion.

No 97140 (SEQ ID NO. 19) 75 bases
5' AATTCAAAAACCGATTTTTGATGAGTG-CAGAAGCTTTTGAACACCTCAA
AACTCAATTCGATTTGAACGCCTGCA 3'

No 97141 (SEQ ID NO. 20) 67 bases
5' GGCGTTCAAATCGAATTGAGTTTTGAG-GTGTTCAAAAGCTTCTGCACTC
ATCAAAAATCGGTTTTTG 3'

-continued

RT-PCR Primers

No 97142 (SEQ ID NO. 21) 25 bases
5' CATGAAAATTGTTTTGGCCATCGCC 3'
EaeI

No 97143 (SEQ ID NO. 22) 24 bases
5' CGGTTTTTGAATTCATCCAACGAC 3'
EcoRI

EXAMPLE 2

Expression in Mammalian Cells pNIV4812, an expression plasmid based on pEE14 (CellTech, Cockett et al., 1990 Biotechnology, vol 8, 662-667) designed to produce the mature form of Der p1 in CHO-K1, codes for a pre-Der p1 followed by the mature Der p1 sequence (no pro-protein).

Ligate: HindIII-XbaI from pEE14

HindIII-PstI oligonucleotides no. 97040 and 97041 whose sequence follows

PstI-XbaI from pNIV4810 (plasmid ATCC 87307)

Sequence of the Oligonucleotides no 97040 (SEQ ID NO. 23)

$^{5'}$AGCTTACCATGAAAATTGTTTTGGC-CATCGCCTCATTGTTGGCATTGAG CGCTGTTTAT-GCTCGTACTAACGCCTGCA$^{3'}$ no 97041 (SEQ ID NO. 24)

$^{5'}$GGCGTTAGTACGAGCATAAACAGCGCT-CAATGCCAACAATGAGGCGAT GGCCAAAA-CAATTTTCATGGTA$^{3'}$

Results

The expression of a protein of an apparent molecular weight of 30 kDa has been detected in several extracts (FIG. 3). No protein has been detected in the culture supernatants (data not shown), which suggests that the protein was not secreted from CHO-K1 cells.

Construction of pNIV4814

Starting from pNIV4812, the following construction is made to replace the cysteine residue from the active site by an alanine residue.

Ligate: AflIII-AseI fragment from pNIV4812.

AseI-TfiI oligonucleotides as in pNIV4819 construction (No. 97121 and 97122)

TfiI—BstEII fragment from pNIV4810 (ATCC 87307)

BstEII—AflI fragment from pNIV4812.

Construction of pNIV4819 and pNIV4814 was made possible, thanks to the discovery that in pNIV4810 the codon encoding isoleucine 6 of the mature protein was ATT instead of ATC as published. This sequence is responsible for the presence of the AseI restriction site.

Construction of pNIV4816

Starting from pNIV4812, designed to expressed in CHO-K1, pNIV4816 has the same deletion as for pNIV4815. This construct results in the production of recombinant properP1 with the deletion of the NAET residues from the junction between the pro and mature protein.

Ligate: XbaI—AflII fragment from pEE14

AflII—EaeI fragment from pNIV4812

EaeI—EcoRI fragment generated by RT-PCR using primers No 97142 and 97143

EcoRI—PstI oligonucleotides No 97140 and 97141 (same oligonucleotides as used in pNIV4815)

PstI—XbaI fragment from pNIV4810.

EXAMPLE 3

Expression in *Drosophila* Cells

Construction of pNIV4827 pNIV4827 has been designed to promote the expression and secretion of mature Der p1 from baculovirus infected insect cells.

Ligate: pAcGP67A vector linearized with PstlI

PstI fragment from pNIV4810 (ATCC 87307)

The expression of Der p1 from pNIV4827 has been demonstrated by western blot.

Construction of pNIV4828 pNIV4828 has been designed to promote the expression and secretion of Proper p1 from baculovirus infected insect cells.

Ligate: SapI-BamHI from pAcGP67A (Pharmingen ref. 21220P)

BamH1-EcoRI 172 bp synthetic fragment

EcoRI-BssSI from pNIV4820

BssSI-SapI from pNIV4827

Sequence of the synthetic fragment:

a) coding oligonucleotide No. 97520 (SEQ ID NO. 25)

$^{5'}$GAT CCC CGG CCG TCA TCG ATC AAA ACT TTT GAA GAA TAC AAA AAA GCC TTC AAC AAA AGT TAT GCT ACC TTC GAA GAT GAA GAA GCT GCC CGT AAA AAC TTT TTG GAA TCA GTA AAA TAT GTT CAA TCA AAT GGA GGT GCC ATC AAC CAT TTG TCC GAT TTG TCG TTG GAT G$^{3'}$ 172 mer b) complementary sequence No. 97521 (SEQ ID NO. 26)

$^{5}$ AAT TCA TCC AAC GAC AAA TCG GAC AAA TGG TTG ATG GCA CCT CCA TTT GAT TGA ACA TAT TTT ACT GAT TCC AAA AAG TTT TTA CGG GCA GCT TCT TCA TCT TCG AAG GTA GCA TAA CTT TTG TTG AAG GCT TTT TTG TAT TCT TCA AAA GTT TTG ATC GAT GAC GGC CGG G$^{3}$ 172 mer The expression of Proper p1 from pNIV4828 has been demonstrated by western blot.

Construction of pNIV4832

This plasmid codes for a Der p1 propeptide followed by the mature Der p1 (Proper p1) sequence and is designed to be expressed in *drosophila* cells.

Ligate: Asp718-BamHI fragment from expression vector pDS47/V5-His (INVITROGEN V4115-20)

Asp718-SpeI synthetic fragment resulting from hybridization of 98023 and 98024 oligonucleotides SpeI-BglII fragment from pNIV4828

Sequences of the Oligonucleotides no. 98023 (SEQ ID NO. 27)

$^{5'}$GTA CCC TTA AGA TGC TA$^{3'}$ no. 98024 (SEQ ID NO. 28)

$^{5'}$CTA GTA GCA TCT TAA GG$^{3'}$

NB: pNIV4828 is a plasmid designed for the isolation of recombinant baculoviruses expressing the pro-Derp 1 fused to gp67 signal peptide.

Results

Transitory expression of pro-DerP1 in *drosophila* cells has been detected (data not shown).

Construction of pNIV4840 pNIV4840 differs from pNIV4832 in that the expression vector used is stable and inducible (pMTNV5-His)

Ligate: Asp718-NotI fragment from pNIV4832

NotI—Asp718 from pMTNV5-His (INVITROGEN V4120-20)

Expression of proDerp 1 in *drosophila* cells has been shown (FIG. 4)

Construction of pNIV4842 pNIV4842 was designed to promote the expression and secretion of Proper p1 from recombinant *drosophila* cells. Proper p1 coding sequence was engineered to impair the cleavage of the propeptide. To achieve this goal, four nucleotide triplets coding for NAET including the cleavage site were deleted.

Ligate: NotI-EcoRI from pNIV4840

EcoRI-PstI synthetic fragment resulting from hybridization of oligonucleotides no. 98136 and no. 98137

PstI-BstEII from pNIV4840

BstEII-NotI from pNIV4840

```
Sequence of the synthetic oligonucleotides

a) Coding sequence
No 98136 (SEQ ID NO. 29)                          75 mer
5' AAT TCA AAA ACC GAT TTT TGA TGA GTG CAG AAG CTT
TTG AAC ACC TCA AAA CTC AAT TCG ATT TGA ACG CCT
GCA 3'

Complementary sequence

No 98137 (SEQ ID NO. 30)                          67 mer
5' GGC GTT CAA ATC GAA TTG
AGT TTT GAG GTG TTC AAA
AGC TTC TGC ACT CAT CAA AAA
TCG GTT TTT G 3'
```

Results

Detection of Der p1 in fusion with its propeptide has been detected in the supernatants after induction (FIG. 5). The sequence of this recombinant mutant DerP1 is given in SEQ ID NO. 4.

Construction of pNIV4843 pNIV4843 has been designed to promote the expression and secretion from recombinant *drosophila* cells of a Proper p1 form in which the cysteine residue of the active site has been mutated to an alanine.

Ligate: NotI-Asp718 from pMT/V5-His

Asp718-PstI from pNIV4832

PstI-TfiI from pNIV4819

TfiI-NotI from pNIV4832

Results

Detection of Der p1 in fusion with its propeptide has been detected in the supernatants after induction (FIG. 6). The sequence of this recombinant mutant DerP1 is given in SEQ ID NO. 5.

EXAMPLE 3

Purification Procedure of Recombinant ProDer p1 Secreted from Recombinant *drosophila* Cells Proteins from the spent culture medium (1 liter) were concentrated at 4° C. by overnight ammonium sulfate precipitation to 60% saturation. After centrifugation at 17000 g during 30 min., the precipitate was resuspended in 20 ml of 20 mM Tris-HCl pH8.0 and dialyzed against 5 liters of the same buffer. Insoluble proteins were discarded by centrifugation at 20000 g during 30 min. The dialysate was loaded onto a Q sepharose XL column (3×1.6 cm, Pharmacia) equilibrated in 20 mM Tris-HCL pH8.0. After washing the column with the same buffer, bound proteins were eluted by steps of 100 mM increases of NaCl concentration. Proper p1 mainly eluted at 200 mM NaCl. Enriched Proper p1 fractions were pooled and loaded onto an hydroxyapatite type 1 column (1×1.6 cm, Biorad) conditioned in 5 mM potassium phosphate buffer pH 7.0. Unbound material containing Proper p1 was concentrated by ultrafiltration using Omega membrane (cut-off: 10 kD, Filtron). The concentrate was loaded onto a superdex 75 FPLC column (30×1 cm, Pharmacia) in PBS pH 7.3. Eluted Proper p1 from the gel filtration column was more than 80% pure.

EXAMPLE 4

Vaccine Formulation

Vaccines comprising the mutant DerP1 or allergens may be formulated with many common adjuvants. One preferred adjuvant system is an oil in water emulsion described below:

The oil in water emulsion adjuvant formulations used in the present invention are made comprising following oil in water emulsion component: 5% Squalene, 5% α-tocopherol, 2.0% polyoxyethylene sorbitan monooleate (TWEEN 80). The emulsions are prepared as a 2 fold concentrate. All examples used in the immunological experiments are diluted with the addition of extra components and diluents to give either a 1× concentration (equating to a squalene:QS21 ratio (w/w) of 240:1) or further dilutions thereof.

Briefly, TWEEN 80 is dissolved in phosphate buffered saline (PBS) to give a 2% solution in the PBS. To provide 100 ml of a two fold concentrate emulsion, 5 ml of DL alpha tocopherol and 5 ml of squalene are vortexed to mix thoroughly. 95 ml of PBS/TWEEN solution is added to the oil and mixed thoroughly. The resulting emulsion is then passed through a syringe needle and finally microfluidised by using an M110S Microfluidics machine. The resulting oil droplets have a size of approximately 145-180 nm (expressed as z av. measured by PCS). The other adjuvant/vaccine components (QS21, 3D-MPL and antigen) are added to the emulsion in simple admixture.

The antigen containing vaccines used herein are formulated either with full dose SB62 adjuvant to give a high squalene:QS21 ratio (240:1) or with a lower amount of SB62 to give a low ratio formulation (48:1). Other vaccines may optionally be formulated with the addition of cholesterol to the oil phase of the emulsion.

These vaccines are assayed in groups of Balb/c mice. Briefly, groups of 10 mice are immunised intramuscularly 2 times at 3 weeks interval with 2 μg mutant allergen combined with oil in water emulsion adjuvant. 14 days following the second immunisation the production of cytokines (IL-4, IL5 and IFN-γ) are analysed after in vitro restimulation of spleen and lymph nodes cells with allergen. Antibody response to wild-type allergen and the isotypic profile induced are monitored by ELISA at 21 days post II and 14 days post IV.

The invention claimed is:

1. A recombinant mutant pro-DerP1 allergen of the DerP1 pre-pro-protein of SEQ ID NO: 1 wherein SEQ ID NO: 1 comprises a cysteine to alanine substitution at amino acid position 132 and wherein said pro-DerP1 allergen is from *Dermatophagoides pteronyssinus*.

2. A therapeutic formulation comprising the recombinant mutant pro-DerP1 allergen as claimed in claim 1 and an adjuvant.

3. The therapeutic formulation as claimed in claim 2, wherein the adjuvant is a preferential stimulator of the Th1-type immune response.

4. The therapeutic formulation as claimed in claim 2, wherein the adjuvant comprises at least one selected from the group consisting of QS21 and 3-O-deacylated monophosphoryl lipid A.

* * * * *

SEQUENCE LISTING

```
<160> NUMBER OF SEQ ID NOS: 31

<210> SEQ ID NO 1
<211> LENGTH: 320
<212> TYPE: PRT
<213> ORGANISM: Artificial Sequence
<220> FEATURE:
<223> OTHER INFORMATION: Recombinant mutant Der p1 including
      pre-protein - Cys 132 to Ala 132

<400> SEQUENCE: 1

Met Lys Ile Val Leu Ala Ile Ala Ser Leu Leu Ala Leu Ser Ala Val
 1               5                  10                  15

Tyr Ala Arg Pro Ser Ser Ile Lys Thr Phe Glu Glu Tyr Lys Lys Ala
            20                  25                  30

Phe Asn Lys Ser Tyr Ala Thr Phe Glu Asp Glu Glu Ala Ala Arg Lys
        35                  40                  45

Asn Phe Leu Glu Ser Val Lys Tyr Val Gln Ser Asn Gly Gly Ala Ile
    50                  55                  60

Asn His Leu Ser Asp Leu Ser Leu Asp Glu Phe Lys Asn Arg Phe Leu
65                  70                  75                  80

Met Ser Ala Glu Ala Phe Glu His Leu Lys Thr Gln Phe Asp Leu Asn
                85                  90                  95

Ala Glu Thr Asn Ala Cys Ser Ile Asn Gly Asn Ala Pro Ala Glu Ile
            100                 105                 110

Asp Leu Arg Gln Met Arg Thr Val Thr Pro Ile Arg Met Gln Gly Gly
        115                 120                 125

Cys Gly Ser Ala Trp Ala Phe Ser Gly Val Ala Ala Thr Glu Ser Ala
    130                 135                 140
```

-continued

```
Tyr Leu Ala Tyr Arg Asn Gln Ser Leu Asp Leu Ala Glu Gln Glu Leu
145                 150                 155                 160

Val Asp Cys Ala Ser Gln His Gly Cys His Gly Asp Thr Ile Pro Arg
                165                 170                 175

Gly Ile Glu Tyr Ile Gln His Asn Gly Val Val Gln Glu Ser Tyr Tyr
            180                 185                 190

Arg Tyr Val Ala Arg Glu Gln Ser Cys Arg Arg Pro Asn Ala Gln Arg
        195                 200                 205

Phe Gly Ile Ser Asn Tyr Cys Gln Ile Tyr Pro Pro Asn Val Asn Lys
    210                 215                 220

Ile Arg Glu Ala Leu Ala Gln Thr His Ser Ala Ile Ala Val Ile Ile
225                 230                 235                 240

Gly Ile Lys Asp Leu Asp Ala Phe Arg His Tyr Asp Gly Arg Thr Ile
                245                 250                 255

Ile Gln Arg Asp Asn Gly Tyr Gln Pro Asn Tyr His Ala Val Asn Ile
            260                 265                 270

Val Gly Tyr Ser Asn Ala Gln Gly Val Asp Tyr Trp Ile Val Arg Asn
        275                 280                 285

Ser Trp Asp Thr Asn Trp Gly Asp Asn Gly Tyr Gly Tyr Phe Ala Ala
    290                 295                 300

Asn Ile Asp Leu Met Met Ile Glu Glu Tyr Pro Tyr Val Val Ile Leu
305                 310                 315                 320


<210> SEQ ID NO 2
<211> LENGTH: 272
<212> TYPE: PRT
<213> ORGANISM: Artificial Sequence
<220> FEATURE:
<223> OTHER INFORMATION: Recombinant mutant Der p1 including pre-protein

<400> SEQUENCE: 2

Met Lys Ile Val Leu Ala Ile Ala Ser Leu Leu Ala Leu Ser Ala Val
 1               5                  10                  15

Tyr Ala Arg Pro Ser Ser Ile Lys Thr Phe Glu Glu Tyr Lys Lys Ala
            20                  25                  30

Phe Asn Lys Ser Tyr Ala Thr Phe Glu Asp Glu Glu Ala Ala Arg Lys
        35                  40                  45

Asn Phe Leu Glu Ser Val Lys Tyr Val Gln Ser Asn Gly Gly Ala Ile
    50                  55                  60

Asn His Leu Ser Asp Leu Ser Leu Asp Glu Phe Lys Asn Arg Phe Leu
65                  70                  75                  80

Met Ser Ala Glu Ala Phe Glu His Leu Lys Thr Gln Phe Asp Leu Asn
                85                  90                  95

Ala Cys Ser Ile Asn Gly Asn Ala Pro Ala Glu Ile Asp Leu Arg Gln
            100                 105                 110

Met Arg Thr Val Thr Pro Ile Arg Met Gln Gly Gly Cys Gly Ser Cys
        115                 120                 125

Trp Ala Phe Ser Gly Val Ala Ala Thr Glu Ser Ala Tyr Leu Ala Tyr
    130                 135                 140

Arg Asn Gln Ser Leu Asp Leu Ala Glu Gln Glu Leu Val Asp Cys Ala
145                 150                 155                 160

Ser Gln His Gly Cys His Gly Asp Thr Ile Pro Arg Gly Ile Glu Tyr
                165                 170                 175

Ile Gln His Asn Gly Val Val Gln Glu Ser Tyr Tyr Arg Tyr Val Ala
            180                 185                 190
```

-continued

```
Arg Glu Gln Ser Cys Arg Arg Pro Asn Ala Gln Arg Phe Gly Ile Ser
        195                 200                 205

Asn Tyr Cys Gln Ile Tyr Pro Pro Asn Val Asn Lys Ile Arg Glu Ala
    210                 215                 220

Leu Ala Gln Thr His Ser Ala Ile Ala Val Ile Ile Gly Ile Lys Asp
225                 230                 235                 240

Leu Asp Ala Phe Arg His Tyr Asp Gly Arg Thr Ile Ile Gln Arg Asp
                245                 250                 255

Asn Gly Tyr Gln Pro Asn Tyr His Ala Val Asn Ile Val Gly Tyr Ser
            260                 265                 270


<210> SEQ ID NO 3
<211> LENGTH: 320
<212> TYPE: PRT
<213> ORGANISM: Artificial Sequence
<220> FEATURE:
<223> OTHER INFORMATION: Recombinant mutant Der p1 including
      pre-protein - His 268 to Ala 268

<400> SEQUENCE: 3

Met Lys Ile Val Leu Ala Ile Ala Ser Leu Leu Ala Leu Ser Ala Val
 1               5                  10                  15

Tyr Ala Arg Pro Ser Ser Ile Lys Thr Phe Glu Glu Tyr Lys Lys Ala
            20                  25                  30

Phe Asn Lys Ser Tyr Ala Thr Phe Glu Asp Glu Glu Ala Ala Arg Lys
        35                  40                  45

Asn Phe Leu Glu Ser Val Lys Tyr Val Gln Ser Asn Gly Gly Ala Ile
    50                  55                  60

Asn His Leu Ser Asp Leu Ser Leu Asp Glu Phe Lys Asn Arg Phe Leu
65                  70                  75                  80

Met Ser Ala Glu Ala Phe Glu His Leu Lys Thr Gln Phe Asp Leu Asn
                85                  90                  95

Ala Glu Thr Asn Ala Cys Ser Ile Asn Gly Asn Ala Pro Ala Glu Ile
            100                 105                 110

Asp Leu Arg Gln Met Arg Thr Val Thr Pro Ile Arg Met Gln Gly Gly
        115                 120                 125

Cys Gly Ser Cys Trp Ala Phe Ser Gly Val Ala Ala Thr Glu Ser Ala
    130                 135                 140

Tyr Leu Ala Tyr Arg Asn Gln Ser Leu Asp Leu Ala Glu Gln Glu Leu
145                 150                 155                 160

Val Asp Cys Ala Ser Gln His Gly Cys His Gly Asp Thr Ile Pro Arg
                165                 170                 175

Gly Ile Glu Tyr Ile Gln His Asn Gly Val Val Gln Glu Ser Tyr Tyr
            180                 185                 190

Arg Tyr Val Ala Arg Glu Gln Ser Cys Arg Arg Pro Asn Ala Gln Arg
        195                 200                 205

Phe Gly Ile Ser Asn Tyr Cys Gln Ile Tyr Pro Pro Asn Val Asn Lys
    210                 215                 220

Ile Arg Glu Ala Leu Ala Gln Thr His Ser Ala Ile Ala Val Ile Ile
225                 230                 235                 240

Gly Ile Lys Asp Leu Asp Ala Phe Arg His Tyr Asp Gly Arg Thr Ile
                245                 250                 255

Ile Gln Arg Asp Asn Gly Tyr Gln Pro Asn Tyr Ala Ala Val Asn Ile
            260                 265                 270

Val Gly Tyr Ser Asn Ala Gln Gly Val Asp Tyr Trp Ile Val Arg Asn
```

-continued

```
        275                 280                 285

Ser Trp Asp Thr Asn Trp Gly Asp Asn Gly Tyr Gly Tyr Phe Ala Ala
    290                 295                 300

Asn Ile Asp Leu Met Met Ile Glu Glu Tyr Pro Tyr Val Val Ile Leu
305                 310                 315                 320


<210> SEQ ID NO 4
<211> LENGTH: 339
<212> TYPE: PRT
<213> ORGANISM: Artificial Sequence
<220> FEATURE:
<223> OTHER INFORMATION: Recombinant mutant Der p1 encoded by pNIV4842

<400> SEQUENCE: 4

Met Leu Leu Val Asn Gln Ser His Gln Gly Phe Asn Lys Glu His Thr
 1               5                  10                  15

Ser Lys Met Val Ser Ala Ile Val Leu Tyr Val Leu Leu Ala Ala Ala
            20                  25                  30

Ala His Ser Ala Phe Ala Ala Asp Pro Arg Pro Ser Ser Ile Lys Thr
        35                  40                  45

Phe Glu Glu Tyr Lys Lys Ala Phe Asn Lys Ser Tyr Ala Thr Phe Glu
    50                  55                  60

Asp Glu Glu Ala Ala Arg Lys Asn Phe Leu Glu Ser Val Lys Tyr Val
65                  70                  75                  80

Gln Ser Asn Gly Gly Ala Ile Asn His Leu Ser Asp Leu Ser Leu Asp
                85                  90                  95

Glu Phe Lys Asn Arg Phe Leu Met Ser Ala Glu Ala Phe Glu His Leu
            100                 105                 110

Lys Thr Gln Phe Asp Leu Asn Ala Cys Ser Ile Asn Gly Asn Ala Pro
        115                 120                 125

Ala Glu Ile Asp Leu Arg Gln Met Arg Thr Val Thr Pro Ile Arg Met
    130                 135                 140

Gln Gly Gly Cys Gly Ser Cys Trp Ala Phe Ser Gly Val Ala Ala Thr
145                 150                 155                 160

Glu Ser Ala Tyr Leu Ala Tyr Arg Asn Gln Ser Leu Asp Leu Ala Glu
                165                 170                 175

Gln Glu Leu Val Asp Cys Ala Ser Gln His Gly Cys His Gly Asp Thr
            180                 185                 190

Ile Pro Arg Gly Ile Glu Tyr Ile Gln His Asn Gly Val Val Gln Glu
        195                 200                 205

Ser Tyr Tyr Arg Tyr Val Ala Arg Glu Gln Ser Cys Arg Arg Pro Asn
    210                 215                 220

Ala Gln Arg Phe Gly Ile Ser Asn Tyr Cys Gln Ile Tyr Pro Pro Asn
225                 230                 235                 240

Ala Asn Lys Ile Arg Glu Ala Leu Ala Gln Thr His Ser Ala Ile Ala
                245                 250                 255

Val Ile Ile Gly Ile Lys Asp Leu Asp Ala Phe Arg His Tyr Asp Gly
            260                 265                 270

Arg Thr Ile Ile Gln Arg Asp Asn Gly Tyr Gln Pro Asn Tyr His Ala
        275                 280                 285

Val Asn Ile Val Gly Tyr Ser Asn Ala Gln Gly Val Asp Tyr Trp Ile
    290                 295                 300

Val Arg Asn Ser Trp Asp Thr Asn Trp Gly Asp Asn Gly Tyr Gly Tyr
305                 310                 315                 320

Phe Ala Ala Asn Ile Asp Leu Met Met Ile Glu Glu Tyr Pro Tyr Val
```

-continued

```
            325                 330                 335

Val Ile Leu


<210> SEQ ID NO 5
<211> LENGTH: 343
<212> TYPE: PRT
<213> ORGANISM: Artificial Sequence
<220> FEATURE:
<223> OTHER INFORMATION: Recombinant mutant Der p1 encoded by pNIV4843

<400> SEQUENCE: 5

Met Leu Leu Val Asn Gln Ser His Gln Gly Phe Asn Lys Glu His Thr
 1               5                  10                  15

Ser Lys Met Val Ser Ala Ile Val Leu Tyr Val Leu Leu Ala Ala Ala
            20                  25                  30

Ala His Ser Ala Phe Ala Ala Asp Pro Arg Pro Ser Ser Ile Lys Thr
        35                  40                  45

Phe Glu Glu Tyr Lys Lys Ala Phe Asn Lys Ser Tyr Ala Thr Phe Glu
    50                  55                  60

Asp Glu Glu Ala Ala Arg Lys Asn Phe Leu Glu Ser Val Lys Tyr Val
65                  70                  75                  80

Gln Ser Asn Gly Gly Ala Ile Asn His Leu Ser Asp Leu Ser Leu Asp
                85                  90                  95

Glu Phe Lys Asn Arg Phe Leu Met Ser Ala Glu Ala Phe Glu His Leu
            100                 105                 110

Lys Thr Gln Phe Asp Leu Asn Ala Glu Thr Asn Ala Cys Ser Ile Asn
        115                 120                 125

Gly Asn Ala Pro Ala Glu Ile Asp Leu Arg Gln Met Arg Thr Val Thr
    130                 135                 140

Pro Ile Arg Met Gln Gly Gly Cys Gly Ser Ala Trp Ala Phe Ser Gly
145                 150                 155                 160

Val Ala Ala Thr Glu Ser Ala Tyr Leu Ala Tyr Arg Asn Gln Ser Leu
                165                 170                 175

Asp Leu Ala Glu Gln Glu Leu Val Asp Cys Ala Ser Gln His Gly Cys
            180                 185                 190

His Gly Asp Thr Ile Pro Arg Gly Ile Glu Tyr Ile Gln His Asn Gly
        195                 200                 205

Val Val Gln Glu Ser Tyr Tyr Arg Tyr Val Ala Arg Glu Gln Ser Cys
    210                 215                 220

Arg Arg Pro Asn Ala Gln Arg Phe Gly Ile Ser Asn Tyr Cys Gln Ile
225                 230                 235                 240

Tyr Pro Pro Asn Ala Asn Lys Ile Arg Glu Ala Leu Ala Gln Thr His
                245                 250                 255

Ser Ala Ile Ala Val Ile Ile Gly Ile Lys Asp Leu Asp Ala Phe Arg
            260                 265                 270

His Tyr Asp Gly Arg Thr Ile Ile Gln Arg Asp Asn Gly Tyr Gln Pro
        275                 280                 285

Asn Tyr His Ala Val Asn Ile Val Gly Tyr Ser Asn Ala Gln Gly Val
    290                 295                 300

Asp Tyr Trp Ile Val Arg Asn Ser Trp Asp Thr Asn Trp Gly Asp Asn
305                 310                 315                 320

Gly Tyr Gly Tyr Phe Ala Ala Asn Ile Asp Leu Met Met Ile Glu Glu
                325                 330                 335

Tyr Pro Tyr Val Val Ile Leu
            340
```

-continued

<210> SEQ ID NO 6
<211> LENGTH: 963
<212> TYPE: DNA
<213> ORGANISM: Artificial Sequence
<220> FEATURE:
<223> OTHER INFORMATION: Nucleotide sequence encoding recombinant mutant Der p1 - Cys 132 to Ala 132

<400> SEQUENCE: 6

```
atgaaaattg ttttggccat cgcctcattg ttggcattga gcgctgttta tgctcgtcca      60

tcatcgatca aaacttttga agaatacaaa aaagccttca acaaaagtta tgctaccttc     120

gaagatgaag aagctgcccg taaaaacttt ttggaatcag taaaatatgt tcaatcaaat     180

ggaggtgcca tcaaccattt gtccgatttg tcgttggatg aattcaaaaa ccgatttttg     240

atgagtgcag aagcttttga acacctcaaa actcaattcg atttgaatgc tgaaactaac     300

gcctgcagta tcaatggaaa tgctccagct gaaatcgatt tgcgacaaat gcgaactgtc     360

actcccattc gtatgcaagg aggctgtggt tcagcttggg ctttctctgg tgttgccgca     420

actgaatcag cttatttggc ttaccgtaat caatcattgg atcttgctga acaagaatta     480

gtcgattgtg cttcccaaca cggttgtcat ggtgatacca ttccacgtgg tattgaatac     540

atccaacata atggtgtcgt ccaagaaagc tactatcgat acgttgcacg agaacaatca     600

tgccgacgac caaatgcaca acgtttcggt atctcaaact attgccaaat ttacccacca     660

aatgtaaaca aaattcgtga agctttggct caaacccaca gcgctattgc cgtcattatt     720

ggcatcaaag atttagacgc attccgtcat tatgatggcc gaacaatcat tcaacgcgat     780

aatggttacc aaccaaacta tcacgctgtc aacattgttg gttacagtaa cgcacaaggt     840

gtcgattatt ggatcgtacg aaacagttgg gataccaatt ggggtgataa tggttacggt     900

tattttgctg ccaacatcga tttgatgatg attgaagaat atccatatgt tgtcattctc     960

taa                                                                   963
```

<210> SEQ ID NO 7
<211> LENGTH: 951
<212> TYPE: DNA
<213> ORGANISM: Artificial Sequence
<220> FEATURE:
<223> OTHER INFORMATION: Nucleotide sequence encoding recombinant mutant Der p1 - NAET deletion

<400> SEQUENCE: 7

```
atgaaaattg ttttggccat cgcctcattg ttggcattga gcgctgttta tgctcgtcca      60

tcatcgatca aaacttttga agaatacaaa aaagccttca acaaaagtta tgctaccttc     120

gaagatgaag aagctgcccg taaaaacttt ttggaatcag taaaatatgt tcaatcaaat     180

ggaggtgcca tcaaccattt gtccgatttg tcgttggatg aattcaaaaa ccgatttttg     240

atgagtgcag aagcttttga acacctcaaa actcaattcg atttgaacgc ctgcagtatc     300

aatggaaatg ctccagctga aatcgatttg cgacaaatgc gaactgtcac tcccattcgt     360

atgcaaggag gctgtggttc atgttgggct ttctctggtg ttgccgcaac tgaatcagct     420

tatttggctt accgtaatca atcattggat cttgctgaac aagaattagt cgattgtgct     480

tcccaacacg gttgtcatgg tgataccatt ccacgtggta ttgaatacat ccaacataat     540

ggtgtcgtcc aagaaagcta ctatcgatac gttgcacgag aacaatcatg ccgacgacca     600

aatgcacaac gtttcggtat ctcaaactat tgccaaattt acccaccaaa tgtaaacaaa     660
```

-continued

```
attcgtgaag ctttggctca aacccacagc gctattgccg tcattattgg catcaaagat     720

ttagacgcat tccgtcatta tgatggccga acaatcattc aacgcgataa tggttaccaa     780

ccaaactatc acgctgtcaa cattgttggt tacagtaacg cacaaggtgt cgattattgg     840

atcgtacgaa acagttggga taccaattgg ggtgataatg gttacggtta ttttgctgcc     900

aacatcgatt tgatgatgat tgaagaatat ccatatgttg tcattctcta a              951
```

<210> SEQ ID NO 8
<211> LENGTH: 963
<212> TYPE: DNA
<213> ORGANISM: Artificial Sequence
<220> FEATURE:
<223> OTHER INFORMATION: Nucleotide sequence encoding recombinant mutant Der p1 - His 268 to Ala 268

<400> SEQUENCE: 8

```
atgaaaattg ttttggccat cgcctcattg ttggcattga gcgctgttta tgctcgtcca      60

tcatcgatca aaacttttga agaatacaaa aaagccttca acaaaagtta tgctaccttc     120

gaagatgaag aagctgcccg taaaaacttt ttggaatcag taaaatatgt tcaatcaaat     180

ggaggtgcca tcaaccattt gtccgatttg tcgttggatg aattcaaaaa ccgatttttg     240

atgagtgcag aagcttttga acacctcaaa actcaattcg atttgaatgc tgaaactaac     300

gcctgcagta tcaatggaaa tgctccagct gaaatcgatt tgcgacaaat gcgaactgtc     360

actcccattc gtatgcaagg aggctgtggt tcatgttggg ctttctctgg tgttgccgca     420

actgaatcag cttatttggc ttaccgtaat caatcattgg atcttgctga acaagaatta     480

gtcgattgtg cttcccaaca cggttgtcat ggtgatacca ttccacgtgg tattgaatac     540

atccaacata atggtgtcgt ccaagaaagc tactatcgat acgttgcacg agaacaatca     600

tgccgacgac caaatgcaca acgtttcggt atctcaaact attgccaaat ttacccacca     660

aatgtaaaca aaattcgtga agctttggct caaacccaca gcgctattgc cgtcattatt     720

ggcatcaaag atttagacgc attccgtcat tatgatggcc gaacaatcat tcaacgcgat     780

aatggttacc aaccaaacta tgctgctgtc aacattgttg gttacagtaa cgcacaaggt     840

gtcgattatt ggatcgtacg aaacagttgg gataccaatt ggggtgataa tggttacggt     900

tattttgctg ccaacatcga tttgatgatg attgaagaat atccatatgt tgtcattctc     960

taa                                                                   963
```

<210> SEQ ID NO 9
<211> LENGTH: 36
<212> TYPE: DNA
<213> ORGANISM: Artificial Sequence
<220> FEATURE:
<223> OTHER INFORMATION: XhoI-PstI oligonucleotide

<400> SEQUENCE: 9

```
tcgagaaaag agaggctgaa gctactaacg cctgca                                36
```

<210> SEQ ID NO 10
<211> LENGTH: 28
<212> TYPE: DNA
<213> ORGANISM: Artificial Sequence
<220> FEATURE:
<223> OTHER INFORMATION: XhoI-PstI oligonucleotide

<400> SEQUENCE: 10

```
ggcgttagta gcttcagcct ctcttttc                                         28
```

-continued

<210> SEQ ID NO 11
<211> LENGTH: 86
<212> TYPE: DNA
<213> ORGANISM: Artificial Sequence
<220> FEATURE:
<223> OTHER INFORMATION: BamHI-PstI oligonucleotide

<400> SEQUENCE: 11
gatccaaacg atgagatttc cttcaatttt tactgcagtt ttattcgcag catcctccgc 60
attagctgct ccaactaacg cctgca 86

<210> SEQ ID NO 12
<211> LENGTH: 78
<212> TYPE: DNA
<213> ORGANISM: Artificial Sequence
<220> FEATURE:
<223> OTHER INFORMATION: BamHI-PstI oligonucleotide

<400> SEQUENCE: 12
ggcgttagtt ggagcagcta atgcggagga tgctgcgaat aaaactgcag taaaaattga 60
aggaaatctc atcgtttg 78

<210> SEQ ID NO 13
<211> LENGTH: 74
<212> TYPE: DNA
<213> ORGANISM: Artificial Sequence
<220> FEATURE:
<223> OTHER INFORMATION: oligonucleotide allowing the NAET deletion

<400> SEQUENCE: 13
aattcaaaaa ccgatttttg atgagtgcag aagcttttga acacctaaaa ctcaattcga 60
tttgaacgcc tgca 74

<210> SEQ ID NO 14
<211> LENGTH: 66
<212> TYPE: DNA
<213> ORGANISM: Artificial Sequence
<220> FEATURE:
<223> OTHER INFORMATION: oligonucleotide allowing the NAET deletion

<400> SEQUENCE: 14
ggcgttcaaa tcgaattgag ttttgaggtg ttcaaaagct tctgcatcat caaaaatcgg 60
tttttg 66

<210> SEQ ID NO 15
<211> LENGTH: 25
<212> TYPE: DNA
<213> ORGANISM: Artificial Sequence
<220> FEATURE:
<223> OTHER INFORMATION: RT-PCR primer

<400> SEQUENCE: 15
catgaaaatt gttttggcca tcgcc 25

<210> SEQ ID NO 16
<211> LENGTH: 24
<212> TYPE: DNA
<213> ORGANISM: Artificial Sequence
<220> FEATURE:
<223> OTHER INFORMATION: RT-PCR primer

<400> SEQUENCE: 16
cggtttttga attcatccaa cgac 24

-continued

<210> SEQ ID NO 17
<211> LENGTH: 113
<212> TYPE: DNA
<213> ORGANISM: Artificial Sequence
<220> FEATURE:
<223> OTHER INFORMATION: AseI-TfiI synthetic fragment

<400> SEQUENCE: 17
taatggaaat gctccagctg aaatcgattt gcgacaaatg cgaactgtca ctcccattcg 60
tatgcaagga ggctgtggtt cagcttgggc tttctctggt gttgccgcaa ctg 113

<210> SEQ ID NO 18
<211> LENGTH: 114
<212> TYPE: DNA
<213> ORGANISM: Artificial Sequence
<220> FEATURE:
<223> OTHER INFORMATION: AseI-TfiI synthetic fragment

<400> SEQUENCE: 18
attcagttgc ggcaacacca gagaaagccc aagctgaacc acagcctcct tgcatacgaa 60
tgggagtgac agttcgcatt tgtcgcaaat cgatttcagc tggagcattt ccat 114

<210> SEQ ID NO 19
<211> LENGTH: 75
<212> TYPE: DNA
<213> ORGANISM: Artificial Sequence
<220> FEATURE:
<223> OTHER INFORMATION: oligonucleotide allowing the NAET deletion

<400> SEQUENCE: 19
aattcaaaaa ccgatttttg atgagtgcag aagcttttga acacctcaaa actcaattcg 60
atttgaacgc ctgca 75

<210> SEQ ID NO 20
<211> LENGTH: 67
<212> TYPE: DNA
<213> ORGANISM: Artificial Sequence
<220> FEATURE:
<223> OTHER INFORMATION: oligonucleotide allowing the NAET deletion

<400> SEQUENCE: 20
ggcgttcaaa tcgaattgag ttttgaggtg ttcaaaagct tctgcactca tcaaaaatcg 60
gtttttg 67

<210> SEQ ID NO 21
<211> LENGTH: 25
<212> TYPE: DNA
<213> ORGANISM: Artificial Sequence
<220> FEATURE:
<223> OTHER INFORMATION: RT-PCR primer

<400> SEQUENCE: 21
catgaaaatt gttttggcca tcgcc 25

<210> SEQ ID NO 22
<211> LENGTH: 24
<212> TYPE: DNA
<213> ORGANISM: Artificial Sequence
<220> FEATURE:
<223> OTHER INFORMATION: RT-PCR primer

<400> SEQUENCE: 22

-continued

```
cggtttttga attcatccaa cgac                                          24


<210> SEQ ID NO 23
<211> LENGTH: 78
<212> TYPE: DNA
<213> ORGANISM: Artificial Sequence
<220> FEATURE:
<223> OTHER INFORMATION: HindIII-PstI oligonucleotide

<400> SEQUENCE: 23

agcttaccat gaaaattgtt ttggccatcg cctcattgtt ggcattgagc gctgtttatg     60

ctcgtactaa cgcctgca                                                  78


<210> SEQ ID NO 24
<211> LENGTH: 70
<212> TYPE: DNA
<213> ORGANISM: Artificial Sequence
<220> FEATURE:
<223> OTHER INFORMATION: HindIII-PstI oligonucleotide

<400> SEQUENCE: 24

ggcgttagta cgagcataaa cagcgctcaa tgccaacaat gaggcgatgg ccaaaacaat     60

tttcatggta                                                           70


<210> SEQ ID NO 25
<211> LENGTH: 172
<212> TYPE: DNA
<213> ORGANISM: Artificial Sequence
<220> FEATURE:
<223> OTHER INFORMATION: BamH1-EcoRI 172 bp synthetic fragment

<400> SEQUENCE: 25

gatccccggc cgtcatcgat caaaactttt gaagaataca aaaaagcctt caacaaaagt     60

tatgctacct tcgaagatga agaagctgcc cgtaaaaact ttttggaatc agtaaaatat    120

gttcaatcaa atggaggtgc catcaaccat ttgtccgatt tgtcgttgga tg            172


<210> SEQ ID NO 26
<211> LENGTH: 172
<212> TYPE: DNA
<213> ORGANISM: Artificial Sequence
<220> FEATURE:
<223> OTHER INFORMATION: BamH1-EcoRI 172 bp synthetic fragment
      complementary sequence

<400> SEQUENCE: 26

aattcatcca acgacaaatc ggacaaatgg ttgatggcac ctccatttga ttgaacatat     60

tttactgatt ccaaaaagtt tttacgggca gcttcttcat cttcgaaggt agcataactt    120

ttgttgaagg ctttttgta ttcttcaaaa gttttgatcg atgacggccg gg            172


<210> SEQ ID NO 27
<211> LENGTH: 17
<212> TYPE: DNA
<213> ORGANISM: Artificial Sequence
<220> FEATURE:
<223> OTHER INFORMATION: 98023 oligonucleotide

<400> SEQUENCE: 27

gtacccttaa gatgcta                                                   17


<210> SEQ ID NO 28
<211> LENGTH: 17
<212> TYPE: DNA
```

-continued

```
<213> ORGANISM: Artificial Sequence
<220> FEATURE:
<223> OTHER INFORMATION: 98024 oligonucleotide

<400> SEQUENCE: 28

ctagtagcat cttaagg                                              17


<210> SEQ ID NO 29
<211> LENGTH: 75
<212> TYPE: DNA
<213> ORGANISM: Artificial Sequence
<220> FEATURE:
<223> OTHER INFORMATION: 98136 oligonucleotide

<400> SEQUENCE: 29

aattcaaaaa ccgatttttg atgagtgcag aagcttttga acacctcaaa actcaattcg     60

atttgaacgc ctgca                                                75


<210> SEQ ID NO 30
<211> LENGTH: 67
<212> TYPE: DNA
<213> ORGANISM: Artificial Sequence
<220> FEATURE:
<223> OTHER INFORMATION: 98137 oligonucleotide

<400> SEQUENCE: 30

ggcgttcaaa tcgaattgag ttttgaggtg ttcaaaagct tctgcactca tcaaaaatcg     60

gtttttg                                                         67


<210> SEQ ID NO 31
<211> LENGTH: 4
<212> TYPE: PRT
<213> ORGANISM: Artificial Sequence
<220> FEATURE:
<223> OTHER INFORMATION: Propeptide cleavage site

<400> SEQUENCE: 31

Asn Ala Glu Thr
 1
```